(12) United States Patent
Hurlimann et al.

(10) Patent No.: US 6,570,382 B1
(45) Date of Patent: *May 27, 2003

(54) NUCLEAR MAGNETIC RESONANCE METHOD AND LOGGING APPARATUS

(75) Inventors: Martin D. Hurlimann, Ridgefield, CT (US); Charles Flaum, Ridgefield, CT (US); Mark Flaum, Ridgefield, CT (US); Lalitha Venkataramanan, Stamford, CT (US)

(73) Assignee: Schlumberger Technology Corporation, Ridgefield, CT (US)

(*) Notice: Subject to any disclaimer, the term of this patent is extended or adjusted under 35 U.S.C. 154(b) by 0 days.

This patent is subject to a terminal disclaimer.

(21) Appl. No.: 09/723,803

(22) Filed: Nov. 28, 2000

Related U.S. Application Data

(63) Continuation of application No. 09/528,881, filed on Mar. 20, 2000.
(60) Provisional application No. 60/170,121, filed on Dec. 10, 1999.

(51) Int. Cl.[7] ................................................ G01V 3/00
(52) U.S. Cl. ...................................... 324/303; 324/306
(58) Field of Search ................................ 324/303, 309, 324/306

(56) References Cited

U.S. PATENT DOCUMENTS

| | | | |
|---|---|---|---|
| 4,734,646 A | 3/1988 | Shenoy et al. ............... | 324/309 |
| 4,986,272 A | * 1/1991 | Reiderer et al. ............. | 600/410 |
| 5,023,551 A | 6/1991 | Kleinberg et al. ........... | 324/303 |
| 5,055,787 A | 10/1991 | Kleinberg et al. ........... | 324/303 |
| 5,055,788 A | 10/1991 | Kleinberg et al. ........... | 324/303 |
| 5,153,514 A | 10/1992 | Griffin et al. ................ | 324/303 |
| 5,212,447 A | 5/1993 | Paltiel ......................... | 324/300 |
| 5,245,282 A | * 9/1993 | Mugler, III et al. ......... | 324/309 |
| 5,363,041 A | 11/1994 | Sezginer ...................... | 324/303 |
| 5,389,877 A | 2/1995 | Sezginer et al. ............. | 324/303 |

(List continued on next page.)

FOREIGN PATENT DOCUMENTS

| EP | WO0097/01110 | * 1/1997 |
|---|---|---|

OTHER PUBLICATIONS

Akkurt, R. et al. *NMR Logging of Natural Gas Reservoirs*. SPWLA 36th Annual Logging Symposium (Jun. 26–29, 1995).

Flaum, Charles et al. *Identification of Gas with the Combinable Magnetic Resonance Tool (CMR\*)*. SPWLA 37th Annual Logging Symposium (Jun. 16–19, 1996).

Prammer, M.G. et al. *Lithology–Independence Gas Detection by Gradient–NMR Logging*, SPE 30562. Prepared for the SPE Annual Tech Conf & Exh., Dallas, Texas (Oct. 22–25, 1995) pp. 325–336.

*Primary Examiner*—Edward Lefkowitz
*Assistant Examiner*—Tiffany A. Fetzner
(74) *Attorney, Agent, or Firm*—Jody Lynn DeStefanis; William B. Batzer; John J. Ryberg

(57) ABSTRACT

NMR methods for extracting information about a fluid in rock and logging apparatuses for implementing such methods in a borehole environment are provided. The methods involve generating at least two different magnetic field pulse sequences. The magnetic field pulse sequences include a first portion and a second portion. A magnetic field pulse sequence is generated, and magnetic resonance signals are detected using the second portion of the sequence. The first portion of the sequence is modified, and again the sequence generated and magnetic resonance signals detected using the second portion. The magnetic resonance signals are analyzed, and information about, for example, diffusion coefficient, viscosity, composition, saturation in a rock, pore size, pore geometry and the like, extracted from the analyzed signals.

67 Claims, 13 Drawing Sheets

U.S. PATENT DOCUMENTS

| | | | | |
|---|---|---|---|---|
| 5,680,043 A | * | 10/1997 | Hurlimann et al. | 324/303 |
| 5,796,252 A | | 8/1998 | Kleinberg et al. | 324/303 |
| 5,936,405 A | | 8/1999 | Prammer et al. | 324/303 |
| 6,005,389 A | * | 12/1999 | Prammer | 324/303 |
| 6,023,163 A | | 2/2000 | Flaum et al. | 324/303 |
| 6,097,184 A | * | 8/2000 | Flaum | 324/303 |
| 6,229,308 B1 | * | 5/2001 | Freedman | 324/303 |
| 6,369,567 B1 | * | 4/2002 | Sone et al. | 324/303 |

* cited by examiner

NUCLEAR MAGNETIC RESONANCE METHOD AND LOGGING APPARATUS

This patent application claims priority from U.S. Provisional Application No. 60/170,121 filed on Dec. 10, 1999 and is a CIP of U.S. application Ser. No. 09/528,881 filed on Mar. 20, 2000, both of which are herein incorporated by reference in their entireties.

FIELD OF THE INVENTION

This invention relates to investigations of rock samples, and more particularly relates to nuclear magnetic resonance (NMR) methods for determining characteristics of subsurface rock, including fluid composition.

BACKGROUND

NMR has been a common laboratory technique for over forty years and has become an important tool in formation evaluation. General background of NMR well logging can be found, for example, in U.S. Pat. No. 5,023,551 to Kleinberg et al., which is assigned to the same assignee as the present invention and herein incorporated by reference in its entirety.

NMR relies upon the fact that the nuclei of many chemical elements have angular momentum ("spin") and a magnetic moment. In an externally applied static magnetic field, the spins of nuclei align themselves along the direction of the static field. This equilibrium situation can be disturbed by a pulse of an oscillating magnetic field (e.g., an RF pulse) that tips the spins away from the static field direction. The angle through which the spins are tipped is given by $\theta=\gamma B_1 t_p/2$, where $\gamma$ is the gyromagnetic ratio, $B_1$ is the linearly polarized oscillating field strength, and $t_p$ is the duration of the pulse. Tipping pulses of ninety and one hundred eighty degrees are most common.

After tipping, two things occur simultaneously. First, the spins precess around the direction of the static field at the Larmor frequency, given by $\omega_0=\gamma B_0$, where $B_0$ is the strength of the static field and $\gamma$ is the gyromagnetic ratio. For hydrogen nuclei, $\gamma/2\pi=4258$ Hz/Gauss, so, for example, in a static field of 235 Gauss, the hydrogen spins would precess at a frequency of 1 MHz. Second, the spins return to the equilibrium direction according to a decay time, $T_1$, which is known as the spin-lattice relaxation time.

Also associated with the spin of molecular nuclei is a second relaxation time, $T_2$, called the spin—spin relaxation time. At the end of a ninety-degree tipping pulse, all the spins are pointed in a common direction perpendicular, or transverse, to the static field, and they all precess at the Larmor frequency. However, because of small fluctuations in the static field induced by other spins or paramagnetic impurities, the spins precess at slightly different frequencies, and the transverse magnetization dephases with a time constant $T_2$.

A standard technique for measuring $T_2$, both in the laboratory and in well logging, uses an RF pulse sequence known as the CPMG (Carr-Purcell-Meiboom-Gill) sequence. As is well known, after a wait time that precedes each pulse sequence, a ninety degree pulse causes the spins to start precessing. Then, a one hundred eighty degree pulse is applied that keeps the spins in the measurement plane, but causes the spins, which are dephasing in the transverse plane, to reverse direction and to refocus. By repeatedly reversing the spins using a series of one hundred eighty degree pulses, a series of "spin echoes" appear. The train of echoes is measured and processed to determine the irreversible dephasing, $T_2$.

In rock formations, such as in a borehole environment, $T_2$ for hydrogen-containing fluids (e.g., water, oil, gas) can have significant contributions due to surface relaxation, bulk relaxation, and diffusion effects, i.e., $$\frac{1}{T_2} = \frac{1}{T_{2,surface}} + \frac{1}{T_{2,bulk}} + \frac{1}{T_{2,diffusion}}. \tag{1}$$

Each of these contributions provides some information about the rock formation and/or about the fluid in the rock formation. For example, in a wetting phase, the surface relaxation contribution, $T_{2,surface}$, dominates the distribution of observed distribution of decay times, $f(T_2)$. Spins relax predominantly due to collisions with the grain surface, with the collision rate being inversely proportional to the pore size. This means that the observed relaxation time is roughly proportional to the pore size, i.e., $1/T_{2,suface}=\rho_s S/V_p$, where S is the surface area of the pore, $V_p$ is the pore volume, and $\rho_2$ is the surface relaxivity of the rock, a phenomenological parameter that indicates how relaxing the surface is. Thus, for a wetting phase, the observed $f(T_2)$ provides information about pore size distribution. In a nonwetting phase, surface relaxation becomes negligible and bulk relaxation, which is related to viscosity, dominates the observed $f(T_2)$. Thus, for a nonwetting phase, the observed $f(T_2)$ provides information about viscosity.

In a uniform static magnetic field, each spin will experience the same magnetic field strength regardless of its position within the static field, and diffusion will not contribute to the observed $f(T_2)$. In a magnetic field gradient, however, each spin will experience different magnetic field strengths as it diffuses through the static field. The Larmor frequencies of the diffusing spins become time dependent, and the series of one hundred eighty degree pulses cannot refocus the spins completely, leading to an additional decay signal. This additional decay signal is proportional to the diffusion coefficient, D, of the fluid and to the square of the gradient strength, g, and the square of the echo spacing, $t_E$, i.e., $$\frac{1}{T_{2,diffusion}} = \frac{1}{12}\gamma^2 g^2 D t_E^2. \tag{2}$$

As the diffusion coefficient provides an indication of fluid type, measurement of the diffusion effects on $f(T_2)$ can be used as the basis for determining the types of fluids in a rock formation.

Certain NMR measurements of diffusion involve changing the echo spacing, $t_E$, in a standard CPMG sequence, and thus the amount of diffusion the spins undergo between echoes, and then comparing the measured relaxations. FIGS. 1A and 1B generally illustrate this approach. FIG. 1A shows two CPMG sequences with different echo spacings, $t_1$ and $t_2$, where $t_2$ is longer than $t_1$. As the echo spacing increases, the spins diffuse further between echoes, and the measured relaxation times will decrease depending on the diffusion coefficient of the fluid, as given in Equation 2 above. FIG. 1B shows the relaxation distributions, $f(T_2)$, for an oil and water determined from the two sets of echoes acquired from the two CPMG sequences illustrated in FIG. 1A. As seen in FIG. 1B, the relaxation distribution with the longer echo spacing, $t_2$, is shifted to lower relaxation times, $T_2$, relative to the relaxation distribution with the shorter echo spacing, $t_1$. The size of the shift is proportional to the size of the diffusion coefficient, as indicated by arrows 1 and 2. The shift of $f(T_2)$ for a fluid with a small diffusion coefficient 1, such as heavy oil, is smaller than the shift for a fluid with a larger diffusion coefficient 2, such as water or natural gas.

While such NMR diffusion measurements can be useful, they suffer from a number of drawbacks. For example, for a given acquisition time, the two CPMG sequences will not have the same number of echoes. The CPMG sequence with longer echo spacing will have a fewer number of echoes available, so will suffer from lower signal to noise and lower data quality in general. In addition, relaxation distributions for different fluids often overlap, at least partially, making it difficult to identify shifts of individual relaxation times. In cases where the diffusion coefficients for different fluids are small, the shifts may be difficult to distinguish. Finally, these methods cannot separate out the contributions due to diffusion effects from the surface and bulk relaxation contributions in the observed relaxation distributions. Surface relaxation and diffusion have similar effects on the observed relaxation distributions, so these methods may provide inaccurate information about the fluid and about the rock or earth formation under investigation.

SUMMARY OF INVENTION

The invention provides in one aspect a method for extracting information about a fluid that may be contained in rock or within a portion of earth formation surrounding a borehole (as used hereinafter, the term "rock" includes earth, earth formation, and a portion of earth formation). For example, certain embodiments of the invention involve generating a sequence of magnetic field pulses in the fluid. The magnetic field pulse sequence includes an initial magnetic field pulse, a first portion that follows the initial magnetic field pulse, and a second portion that follows the first portion. Magnetic resonance signals are detected using the second portion. The first portion of the sequence is then modified, and the magnetic field pulse sequence generated and magnetic resonance signals detected using the second portion again. The magnetic resonance signals are analyzed from a time relative to the initial magnetic field pulse, and information about the fluid extracted.

A second aspect of the invention provides a logging apparatus for implementing embodiments of the inventive measurements in a borehole environment. One embodiment of such a logging apparatus includes a logging tool that is moveable through a borehole and a processor coupled with the logging tool. The processor is programmed with instructions which, when executed by the processor, cause the logging tool to generate a sequence of magnetic field pulses in a region of investigation of earth formation surrounding the borehole. The magnetic field pulse sequence includes an initial magnetic field pulse, a first portion, and a second portion. The processor causes the logging tool to detect magnetic resonance signals produced from the region of investigation using the second portion of the sequence, and then modify the first portion of the sequence and repeat generating the sequence and detecting magnetic resonance signals. The programmed instructions also cause the processor to analyze magnetic resonance signals from a time relative to the initial magnetic field pulse and extract information about the region of investigation.

Further details, features and embodiments of the invention will become more readily apparent from the detailed description that follows.

BRIEF DESCRIPTION OF FIGURES

The invention will be described in more detail below in conjunction with the following Figures, in which.

DETAILED DESCRIPTION

A NMR measurement according to the invention involves generating at least two different magnetic field pulse sequences in a fluid and detecting magnetic resonance signals produced by the different magnetic field pulse sequences. Information, such as saturation, diffusion coefficient, viscosity, composition, etc., about a fluid, e.g., in a rock sample or in a rock formation surrounding a borehole, is extracted by analyzing the different magnetic resonance signals.

Generally speaking, the magnetic field pulse sequences used in the invention can be characterized as having two portions, a first portion followed by a second portion. In a NMR measurement according to the invention, the sensitivity of the first portion to diffusion effects in the presence of a magnetic field gradient is modified while the second portion remains substantially the same. Magnetic resonance signals are detected using the second portion and analyzed. Signals detected using the second portion, which is not changed, will exhibit substantially the same relaxation distribution from one magnetic field pulse sequence to the next, except that the amplitude of the signals will have been altered as a result of the first portion having been modified. By analyzing how the magnetic resonance signals change as the first portion is modified, information about the fluid may be extracted.

Stated another way, in the presence of a magnetic field gradient, the first portion of the magnetic field pulse sequences used in the invention are sensitive to both relaxation and diffusion effects whereas the second portion has substantially the same sensitivity to relaxation effects but reduced sensitivity to diffusion effects. Diffusion effects during the first portion introduce an extra decay into the signal detected using the second portion. The signal detected using the second portion is thus attenuated, or "diffusion edited" in proportion to the diffusion coefficient of the fluid (see Equation 2, above).

These diffusion effects may be detected in the presence of a static magnetic field gradient, or with the use of pulsed field gradients as described, for example, in U.S. Pat. No. 5,796,252 to Kleinberg et al., which is assigned to the same assignee as the present invention and incorporated herein by reference in its entirety. Pulsed field gradients introduced into the first portion of the magnetic field pulse sequences of the invention also may be used in conjunction with a static magnetic field to enhance these diffusion effects.

Figure 1A:
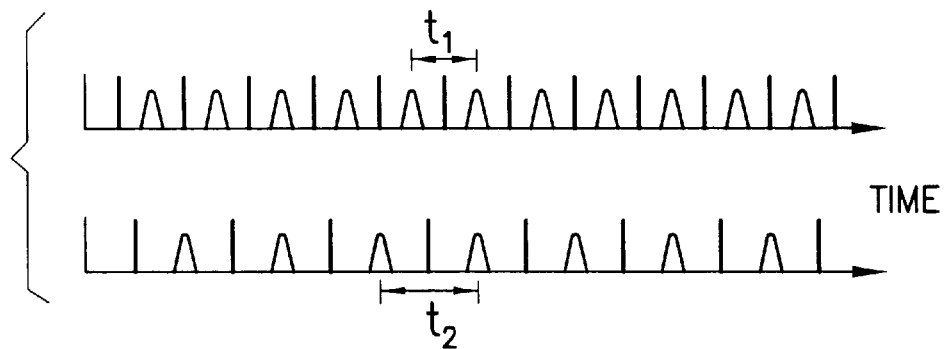
FIGS. 1A and 1B, taken together, illustrate a NMR measurement and $T_2$ distributions obtained therefrom according to the prior art.
Figure 1B:
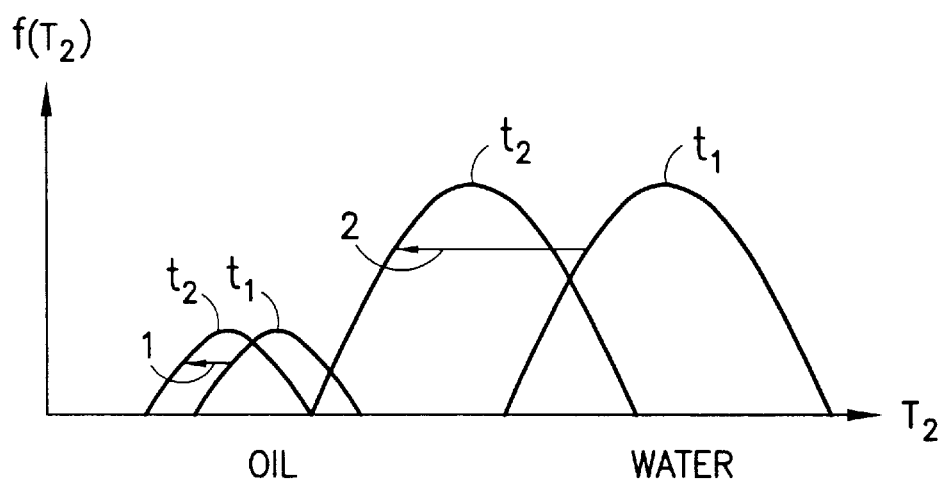
Figure 2A:
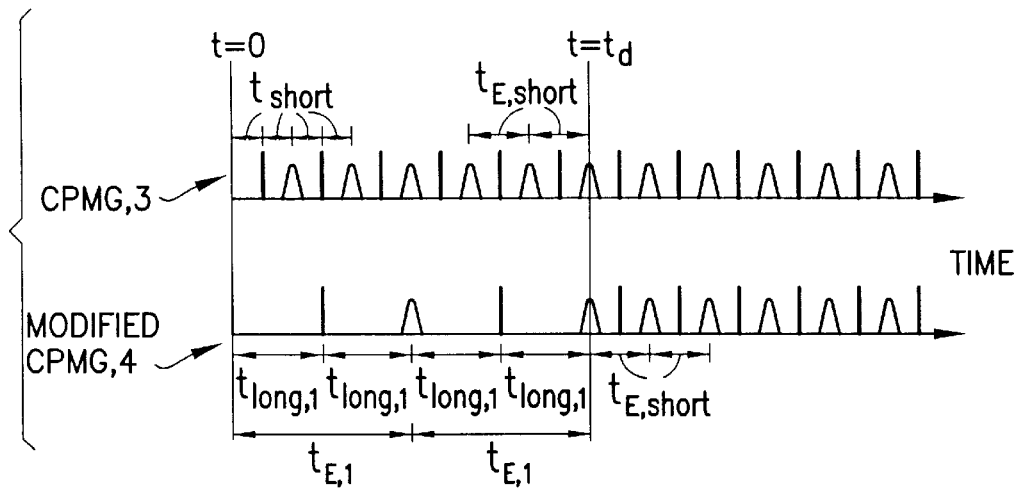
FIGS. 2A and 2B, taken together, illustrate one embodiment of a NMR measurement and $T_2$ distributions obtained therefrom according to the invention.
Figure 2B:
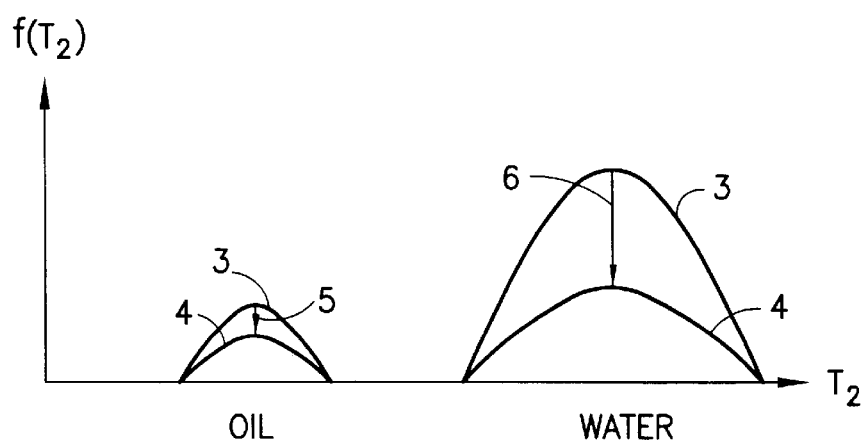

FIGS. 2A and 2B illustrate one embodiment of a NMR measurement according to the invention. After a static magnetic field is generated in a fluid in a rock, a first magnetic field pulse sequence 3 and then a second magnetic field pulse sequence 4 are generated in the fluid. The first sequence 3 in this embodiment (shown at the top of FIG. 2A) is a standard CPMG sequence in which an initial 90-degree pulse is followed, after a time $t_{short}$, by a series of 180-degree pulses separated in time by about $2t_{short}$. A magnetic resonance spin echo appears a time $t_{short}$ after each 180-degree pulse, producing a series of magnetic spin echoes with a time spacing, $t_{E,short}$, approximately equal to $2t_{short}$. This first sequence may be represented as:

$$90-[t_{short}-180-t_{short}-echo_i]_n \quad (3)$$

where the time separating the echoes, $t_{E,short}$, is equal to about $2t_{short}$; $echo_i$ is the $i^{th}$ magnetic resonance spin echo; and n is the number of spin echoes in the sequence.

A standard CPMG sequence may be characterized as a magnetic field pulse sequence according to the invention in which the first portion is substantially identical to the second portion. A modified CPMG sequence according to the invention may be thought of as a CPMG sequence in which the first portion has been modified. The second portion of the modified CPMG sequence is not changed and so generates a CPMG-like series of magnetic resonance spin echoes with a time spacing approximately equal to $t_{E,short}$.

The second sequence 4 (shown at the bottom of FIG. 2A) is an embodiment of a modified CPMG sequence 4 in which the first few echo spacings of the standard CPMG sequence are elongated. An initial 90-degree pulse is followed by a first portion containing a first series of 180-degree pulses that begins a time, $t_{long,1}$, after the initial 90-degree pulse and are separated by about $2t_{long,1}$, where $t_{long,1}$ is greater than $t_{short}$. A magnetic resonance spin echo appears at a time $t_{long,1}$ after each 180-degree pulse, producing a first series of magnetic resonance spin echoes with a time spacing $t_{E,1}$ approximately equal to $2t_{long,1}$. The first portion is followed a second portion containing a second series of 180-degree pulses separated in time by about $2t_{short}$. The second series of 180-degree pulses begins at a time $t_{short}$ after the last spin echo of the first portion and refocuses this last spin echo to produce a second series of magnetic resonance spin echoes having a time spacing, $t_{E,short}$, which is equal to about $2t_{short}$.

The embodiment of a modified CPMG sequence 4 shown at the bottom of FIG. 2A may be represented generally as:

$$90-[t_{long,j}-180-t_{long,j}-echo_{k,j}]_{m,j}-[t_{short}-180-t_{short}-echo_{i',j}]_{n',j} \quad (4)$$

where, for the $j^{th}$ sequence, $t_{long,j}$ is greater than $t_{short}$; $echo_{k,j}$ is the $k^{th}$ magnetic resonance spin echo of the first portion; (m,j) is the number of spin echoes of the first portion; $echo_{i',j}$ is the $i'^{th}$ magnetic resonance spin echo of the second portion; and (n',j) is the number of spin echoes of the second portion. As shown in FIG. 2A, the first portion of the modified CPMG sequence 4 contains two spin echoes, i.e., (m,j)=2; it will be appreciated, however, that the first portion may have other numbers of echoes.

Figure 3:
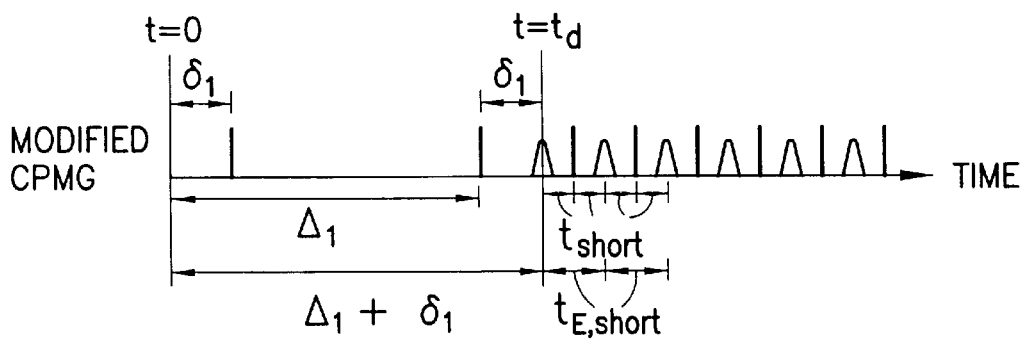
FIG. 3 shows a modified CPMG sequence that can be used in a NMR measurement according to embodiments of the invention.

Another embodiment of a modified CPMG sequence that may be used in accordance with the invention has a first portion that contains a stimulated echo sequence. For example, as shown in FIG. 3, the first portion includes a series of two 90-degree pulses at times $\delta_1$ and $\Delta_1$ after an initial 90-degree pulse, producing a stimulated echo at a time $(\Delta_1+\delta_1)$ after the initial 90-degree pulse. The second portion, which follows the first portion, contains a series of 180-degree pulses which begins a time $t_{short}$ after the last stimulated echo, refocusing the stimulated echo to produce a series of magnetic resonance spin echoes having a time spacing, $t_{E,short}$, which is equal to about $2t_{short}$. The overall sequence may be represented generally as:

$$90-[\delta_j-90-(\Delta_j-\delta_j)-90-\delta_j-echo_{k,j}]_{m,j}-[t_{short}-180-t_{short}-echo_{i',j}]_{n',j} \quad (5)$$

where, for the $j^{th}$ sequence, $echo_{k,j}$ is the $k^{th}$ stimulated echo of the first portion; (m,j) is the number of stimulated echoes of the first portion having an echo spacing equal to about $(\Delta_j+\delta_j)$; and $\delta_j$, $\Delta_j$, $t_{short}$, and indices (i',j) and (n',j) are as defined above.

Other embodiments of a modified CPMG sequence that may be used in accordance with the invention are described in U.S. application Ser. No. 09/528,881, filed on Mar. 20, 2000, which is incorporated herein by reference.

The graph in FIG. 2B represents the relaxation distributions extracted from the magnetic resonance signals detected using the second portions of the first sequence 3 and the second sequence 4 in the presence of a magnetic field gradient. The relaxation distributions, $f(T_2)$, for an oil and water, shown in FIG. 2B are identical except that the amplitude of the second sequence signal 4 is attenuated relative to the amplitude of the first sequence signal 3. The amount of the signal attenuation is proportional to the size of the diffusion coefficient, as indicated by arrows 5 and 6. Thus, the signal attenuation for a fluid with a small diffusion coefficient 5, such as oil, is smaller than the signal attenuation for a fluid with a larger diffusion coefficient 6, such as water or natural gas. Measuring the relative change in amplitude between corresponding spin echoes from the first sequence and from the second sequence can yield quantitative information about the fluid in the sample under investigation.

Typically, the echo spacing in the second portion, $t_{E,short}$, is chosen to be as short as possible to increase the number, n, of spin echoes that can be generated and detected within a given acquisition time. This, in general, increases the signal-to-noise of the measured signal and, in the presence of a magnetic field gradient, reduces the sensitivity of the second portion to diffusion effects. Times for $t_{short}$ on the order of about 0.1 milliseconds (100 µs), leading to echo spacings, $t_{E,short}$, on the order of about 0.2 ms (200 µs), are currently used in well logging measurements, although the measurements of the invention may be made using other times for $t_{short}$ and $t_{E,short}$.

To properly correlate the spin echoes from the first sequence with the spin echoes from the second sequence, the data processing for both sequences starts at the same time, $t_d$, relative to the initial 90-degree pulse. In other words, spin echoes that precede $t_d$ are not used in processing, and only spin echoes starting from $t_d$ are analyzed. By beginning the data processing at the same time for each sequence, the magnetic resonance signals from each sequence will reflect substantially similar relaxation effects.

As shown in FIG. 2A, $t_d$ corresponds to the last echo of the first portion of the modified CPMG sequence. For example, with $t_{short}$=0.1 ms and $t_{long,j}$=4 ms, data processing would start at $t_s$=16 ms, and if the two spin echoes of the first portion of the second sequence are disregarded, then the first 80 spin echoes of the first sequence, i.e., echo$_i$ from i=1 to (m,j)×($t_{long,j}/t_{short}$), would be disregarded. Data processing according to the certain embodiments of the invention, however, may include the last echo of the first portion, i.e., the echo from the first portion that is refocused by the magnetic pulses of the second portion. This means that the spin echoes that occur at t=$t_d$ would be included in the data processing.

Both sequences also may be truncated at the end during processing so a substantially equal number of spin echoes are analyzed and/or echoes with poor signal-to-noise are disregarded. Typically, both sequences still will contain a large number of echoes, particularly as compared to prior art techniques in which the echo spacing of a standard CPMG is increased. Thus, the methods of the invention will generally allow more precise measurements and provide better signal-to-noise as compared to prior art techniques.

Though the spin echoes preceding $t_d$ typically are not used in the above analysis, they may be collected and analyzed to extract other information, such as total porosity, permeability, etc. of a fluid-containing rock sample, as described, for example, in U.S. Pat. Nos. 5,023,551, 5,363,041, and 5,389,877. Such analyses may be done in conjunction with the methods of this invention.

A diffusion edited signal generated according to (4), for times$\geq t_d$, may be represented as:

$$M(t_{E,j}, t) = \int\int dDdT_2 f(D, T_2)\exp\left(-\frac{t}{T_2}\right)\exp\left(-\frac{(m,j)}{12}\gamma^2 g^2 D t_{E,j}^3\right), \quad (6)$$

where $t_d$ corresponds to the time (relative to the initial pulse) of the last echo of the first portion, $f(D,T_2)$ is the two-dimensional diffusion-$T_2$ probability density function, (m,j) is the number of echoes of the first portion, $\gamma$ is the gyromagnetic ratio, g is the gradient field strength, D is the diffusion coefficient, and $t_{E,j}$ is the echo spacing in the first portion of the modified sequence. For modified sequences having more than one echo in the first portion, i.e., (m,j)>1, multiexponential diffusion decays may be observed over a broad detection bandwidth. Such multiexponential decay can be modeled more accurately by replacing the single exponential diffusion attenuation term in Equation 6 with multiple terms. For example, for (m,j)=2, two exponential terms, one from the direct echo and the other from the stimulated echo, would replace the single exponential term in Equation 6, yielding:

where A and B are parameters that depend only on the detection bandwidth.

Similarly, a diffusion edited signal generated according to (5), for times$\geq t_d$, may be represented as:

$$M_{t_d}(\delta, t) = \frac{1}{2}\int\int dDdT_2 f(D(t_d), T_2)\exp\left(-\frac{t}{T_2}\right)\exp(-\gamma^2 g^2 D(t_d) t_d \delta^2), \quad (8)$$

where $t_d$ is the time (relative to the initial pulse) of the stimulated echo, $f(D(t_d),T_2)$ is the two-dimensional diffusion-$T_2$ probability density function at time $t_d$, and $D(t_d)$ represents the diffusion coefficient at time $t_d$.

The amplitude of the detected echoes can be measured using any of various signal processing techniques known in the art and then, according to certain embodiments of the invention, fit to one of Equation 6, 7, 8, or other diffusion edited signal equations, depending on the magnetic pulse sequence used, in order to extract diffusion coefficient and other information about the fluid.

As previously suggested, measuring the relative change in amplitude between corresponding spin echoes from the first and second magnetic field pulse sequences can provide quantitative information about the fluids in the sample under investigation. In particular, a comparison of corresponding spin echoes can separate different contributions to the $T_2$ relaxation distribution, and so yield more accurate information about the fluid. For example, as discussed with regards to FIG. 2A, in the presence of a magnetic field gradient, the first portion of the modified CPMG sequences of the invention are more sensitive to diffusion effects than the second portion, leading to the signal from the second portion to be attenuated, or diffusion-edited, compared to the standard CPMG signal. However, the signal from the second portion exhibits the same surface and bulk relaxation effects as, and is otherwise identical to, the signal from the standard CPMG sequence. Thus, taking a ratio of the amplitudes of the corresponding $T_2$ distributions of the first and second sequences separates diffusion effects from both surface and bulk relaxation effects.

Figure 4:
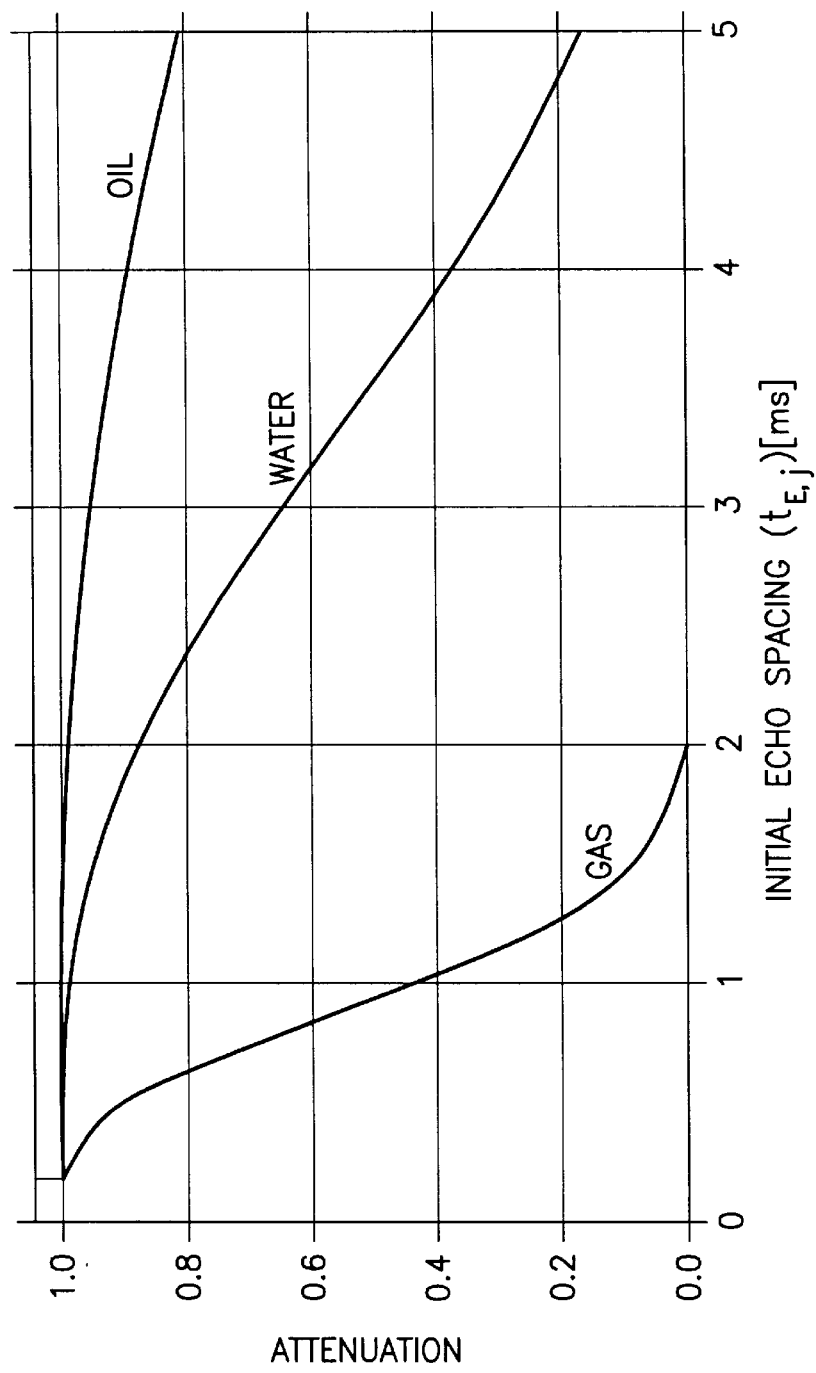
FIG. 4 is a graph of attenuation versus initial echo spacing for three different fluids according to certain embodiments of the invention.

For multiphase fluids, linear mixing laws govern the observed signal attenuation. Thus, components of the fluid having different diffusion coefficients may be differentiated by appropriately selecting and varying a time spacing in the first portion of the modified sequences (e.g., $t_{E,1}$; $\delta_j$ or $\Delta_j$). FIG. 4 contains a graph that may be useful in selecting a first portion time spacing. The graph shows approximate attenuation versus initial echo spacing, $t_{E,1}$, for oil (having a diffusion coefficient, $D_{oil}$, of $2.3\times10^{-6}$ cm$^2$/s), water ($D_{water}$=$2.3\times10^{-5}$ cm$^2$/s) and gas ($D_{gas}$=$1.2\times10^{-3}$ cm$^2$/s) measured in a magnetic field gradient of about 25 Gauss/cm with a modified sequence generated according to (4), having two echoes in the first portion. Over a range of echo spacings greater than approximately 0.8 ms, the relative attenuation of the gas signal is much larger than for either water or oil, indicating that this range may be useful in differentiating gas from water or oil. In general, an initial echo spacing in a range of between about 0.5 to about 20 ms may be useful for hydrocarbon typing applications of the invention.

$$M(t_{E,j}, t) = \int\int dDdT_2 f(D, T_2)\exp\left(-\frac{1}{T_2}\right)\left[A\exp\left(-\frac{1}{6}\gamma^2 g^2 D t_{E,j}^3\right) + B\exp\left(-\frac{1}{3}\gamma^2 g^2 D t_{E,j}^3\right)\right], \quad (7)$$

An initial echo spacing to differentiate between two diffusing components may be approximated as:

$$t_{E,j} \approx \left[ \frac{6\ln\left(\frac{D_+}{D_-}\right)}{\gamma^2 g^2 (D_+ - D_-)} \right]^{1/3}, \quad (9)$$

where $D_+$ is the diffusion coefficient of the higher diffusing component, $D_-$ is the diffusion coefficient of the lower diffusing component, $\gamma$ is the gyromagnetic ratio and g is the magnetic field gradient strength. Equation 9 may provide a useful starting point in selecting an initial time spacing, if the different diffusing components (or a range of diffusion coefficients) are known or can be approximated a priori.

In some embodiments of the invention, the relative attenuation of the echo signal may be quantified in terms of an attenuation factor, $a_j$. The fluid composition then may be determined by taking a linear combination of the attenuation factors for the individual components. For example, the attenuation factor may be calculated as a ratio of the sums of all the measured echoes of a modified CPMG sequence to the measured echoes of a standard CPMG sequence, or as a ratio of initial amplitudes of a modified CPMG sequence to a standard CPMG sequence. In a gradient field of about 25 Gauss/cm and using a modified sequence generated according to (4) with two echoes in the first portion ($t_{E,1}$=8 ms, $t_{E,short}$=0.2 ms), an attenuation factor for bulk water, $a_w$, was calculated to be about 0.32 and for 6 cp oil, $a_{oil}$ was calculated to be about 0.85. For a fluid having water and oil components, the water saturation, $S_w$, i.e., the proportion of fluid that is water, can be determined from the measured attenuation factor of the fluid, $a_{meas}$, using the following relationship:

$$S_w = \frac{a_{oil} - a_{meas}}{a_{oil} - a_w}. \quad (10)$$

Figure 5:
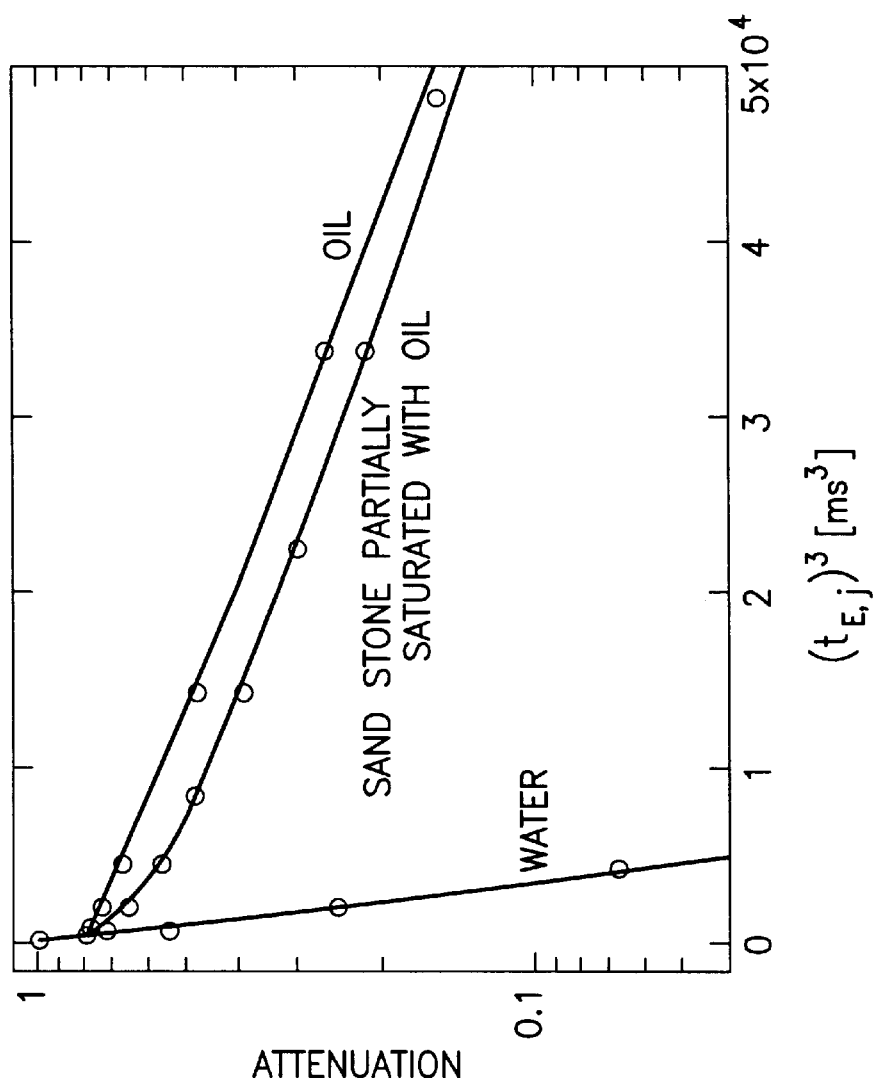
FIG. 5 is a graph showing relative signal attenuations for three samples as initial echo spacing is varied according certain embodiments of the invention.

According to other embodiments, the fluid composition can be determined by fitting the measured attenuation curve versus a first portion time spacing as a superposition of component curves. FIG. 5 shows the relative initial attenuations of diffusion edited signals as an initial echo spacing is changed for a NiCl-doped water sample (labeled "water"), a S6 oil sample (labeled "oil"), and a partially oil saturated sandstone sample. The diffusion edited signals were generated in a uniform gradient field of about 13 Gauss/cm with a modified CPMG sequence according to (4) and having two echoes in the first portion. For the water and oil samples, the plotted points, representing the amplitude of a modified CPMG signal relative to a standard CPMG signal, were fit to a curve using Equation 7 above, with A=0.59 and B=0.20. From the fit, the diffusion coefficients were extracted and found to be $D_w$=2.5×10$^{-5}$ cm$^2$/s for the water sample and $D_{oil}$=1.35×10$^{-6}$ cm$^2$/s for the oil sample. For the partially oil saturated sandstone sample, the relative attenuation was modeled as a superposition of two curves using Equation 7 and three parameters: $S_w$, the water saturation; $D_{w,eff}$, the effective diffusion coefficient for water; and $D_{oil,eff}$, the effective diffusion coefficient for oil. From the fit, it was determined that: $S_w$=0.21, $D_{w,eff}$=1.9×10$^{-5}$ cm$^2$/s, and $D_{oil,eff}$=1.3×10$^{-6}$ cm$^2$/s.

The water saturation, $S_w$, determined in this manner agreed with independent gravitmetrical measurements, and the effective oil diffusion coefficient $D_{oil,eff}$ matched the bulk diffusion coefficient $D_{oil}$ of the pure fluid, as expected. The effective water diffusion coefficient $D_{w,eff}$, however, was smaller than the bulk diffusion coefficient, $D_w$, of water. This difference in water diffusion coefficients is attributed to restricted diffusion of the water in the rock, as water in sandstone is known to mainly occupy the small pores of the rock.

The effects of pore geometry, in terms of restricted diffusion and internal gradients, may be addressed using the methods described in U.S. application Ser. No. 09/528,881. The effects of restricted diffusion and internal gradients may also be addressed in terms of the measured attenuation factor. A hypothetical water saturation for water that does not contribute to the observed signal attenuation, calculated as, e.g., $$S_{w,restr} = \frac{a_{meas} - a_w}{1 - a_w},$$

and a ratio of the measured attenuation factor to that of bulk water, i.e., $$\frac{a_{meas}}{a_w},$$

may be used to correct for the effects of restricted diffusion and internal gradients, respectively, in calculating, for example, water/oil saturation in a rock sample.

The diffusion editing embodiments of the invention thus can extract saturation and diffusion coefficient information about a fluid directly without a priori knowledge of, and without having to make any assumptions about, relaxation in the fluid. As the measurements of these embodiments take place in the presence of a magnetic field gradient, the spin echoes are generated from a thin slice across the sample. By moving the sample and the gradient relative to one another along the gradient direction, an attribute profile of the fluid, for example, a saturation profile of a fluid in a rock sample, can be obtained.

In other embodiments of the invention, a plurality of magnetic field pulse sequences, each with a different first portion (e.g., different time spacing, $t_{long,j}$; or $\delta_j$ and/or $\Delta_j$), are used in making the NMR measurements. The diffusion edited magnetic resonance signal depends on a time spacing in the first portion (e.g., $t_{E,j}$; $\delta_j$, $\Delta_j$), so fluids with different diffusion coefficients will diffuse different amounts during different time spacings (see Equations 6, 7, or 8, above). Inverting data using only two different time spacings (as described in the embodiments above) yields an average diffusion coefficient for every relaxation time and so may not resolve different diffusing components that have overlapping relaxation times. Measuring magnetic resonance signals using more than two different time spacings allows diffusion coefficient and relaxation time to be extracted separately and so can help resolve different fluid components in terms of diffusion and relaxation, as well as other parameters that may be derived from D, $T_2$, or a combination of D and $T_2$, such as $T_1$, viscosity, saturation, porosity, etc.

Figure 6:
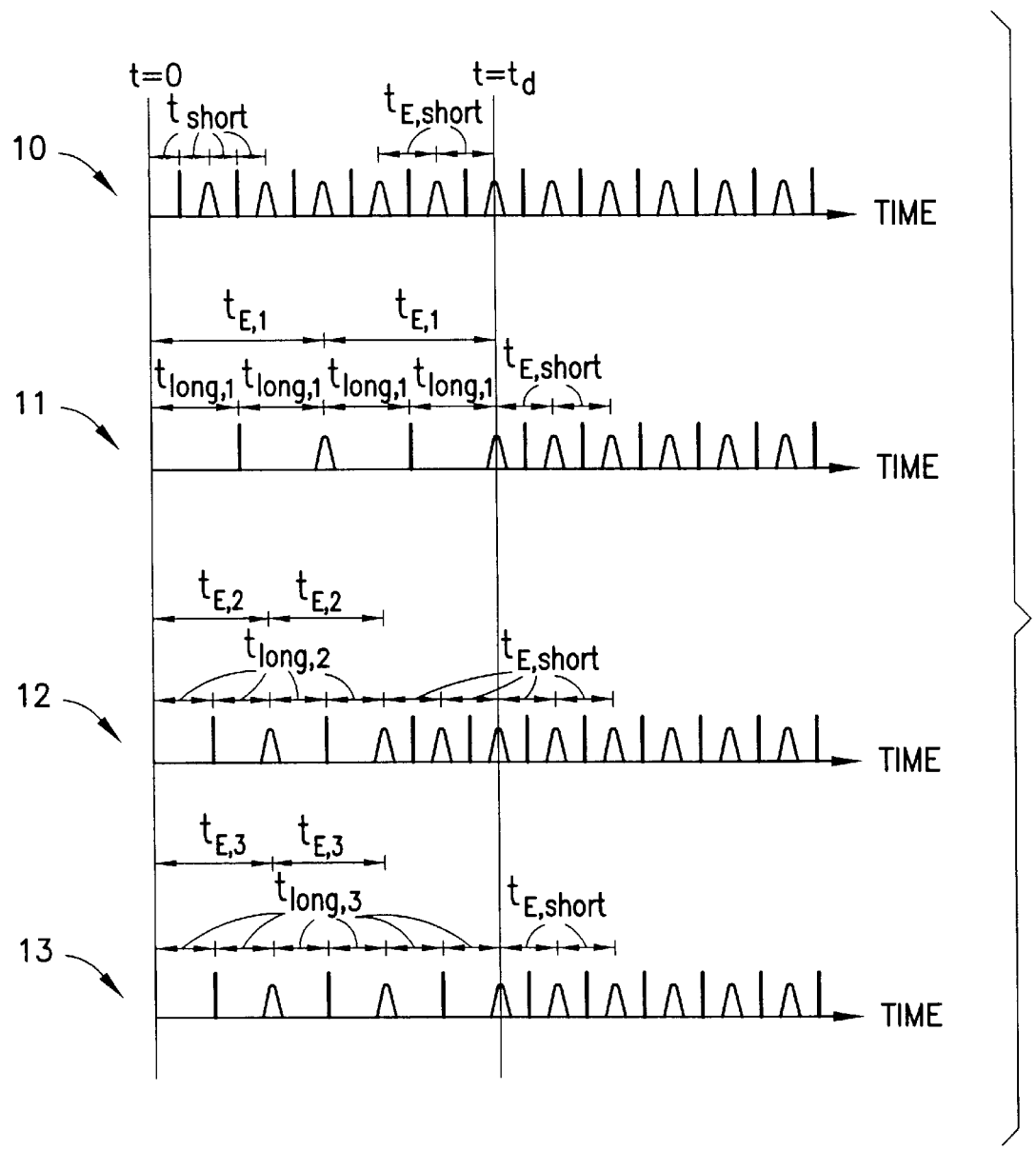
FIG. 6 illustrates a plurality of magnetic field pulse sequences that can be used in one embodiment of a NMR measurement according to the invention.

FIG. 6 illustrates a plurality of magnetic field pulse sequences that may be used in one embodiment of a NMR measurement according to the invention. A first magnetic field pulse sequence 10 is a standard CPMG sequence having a first time spacing, $t_{short}$, and a first echo spacing, $t_{E,short}$. A second magnetic field pulse sequence 11 is generated by modifying, in this case elongating, a time spacing between the initial 90-degree pulse and the first 180-degree pulse, $t_{long,1}$, leading to an elongated echo spacing, $t_{E,1}$, in the first portion. A third magnetic field pulse sequence 12 is generated by modifying a time spacing of the first portion again, $t_{long,2}$. A fourth magnetic field pulse sequence 13 is again generated by modifying a time spacing of the first portion, $t_{long,3}$, and also the number of spin echoes in the first portion.

This embodiment of a NMR measurement involves generating each of the magnetic field pulse sequences shown in FIG. 6 in a fluid in a rock. Magnetic resonance signals from each sequence are detected using the second portion of each sequence, which remains substantially the same from sequence to sequence. As discussed above, to properly correlate the spin echoes detected from each sequence, the data processing for each sequence starts at a time $t_d$ relative to the initial 90-degree pulse. FIG. 6 shows $t_d$ corresponding to the time of the last echo of the second sequence 11, which corresponds in this illustration with the time of the last echo of the fourth sequence 13. Some spin echoes from the second portion of the third sequence 12, which arise prior to time $t_d$, are discarded in the data processing according to this embodiment. The time $t_d$ need not necessarily correspond with the time of the last echo of the longest first portion, as shown in FIG. 6; however, $t_d$ typically is at least as long as the longest first portion.

Although FIG. 6 shows four magnetic field pulse sequences, other numbers of magnetic field pulse sequences may be used in NMR measurements according to the invention, with the use of more sequences resulting in higher resolution in the diffusion (or relaxation, viscosity, saturation, etc.) distribution. Additionally, the plurality of magnetic field pulse sequences need not include one type of modified CPMG sequence, as shown in FIG. 6. Measurements according to methods of the invention may be made using a plurality of magnetic field pulse sequences that includes a combination of modified CPMG sequences generated according to (4), (5) or any of the other sequences described in U.S. application Ser. No. 09/528,881.

The magnetic resonance signals from a plurality of magnetic field pulse sequences may be used to extract a two-dimensional map of any two parameters indicative of the fluid in the rock that can be transformed out of the data, such as D, $T_1$, $T_2$, viscosity, saturation, etc. The measured data may include thousands of data points or, in some cases, tens of thousands of data points or more. In such cases, it may be helpful to compress the data before extracting information about the fluid in the rock.

The two-dimensional density function, $f(D,T_2)$, may be extracted from Equation 6, 7, or 8, above, using, for example, a least-squares optimization process and then plotted to generate a two-dimensional map of diffusion coefficient versus relaxation time. Other parameters, such as viscosity, saturation, porosity, etc., may be derived from D and/or $T_2$, and two such parameters mapped against one another to generate a two-dimensional map of, for example, $T_1$ versus $T_2$, viscosity versus saturation, etc.

Figure 7:
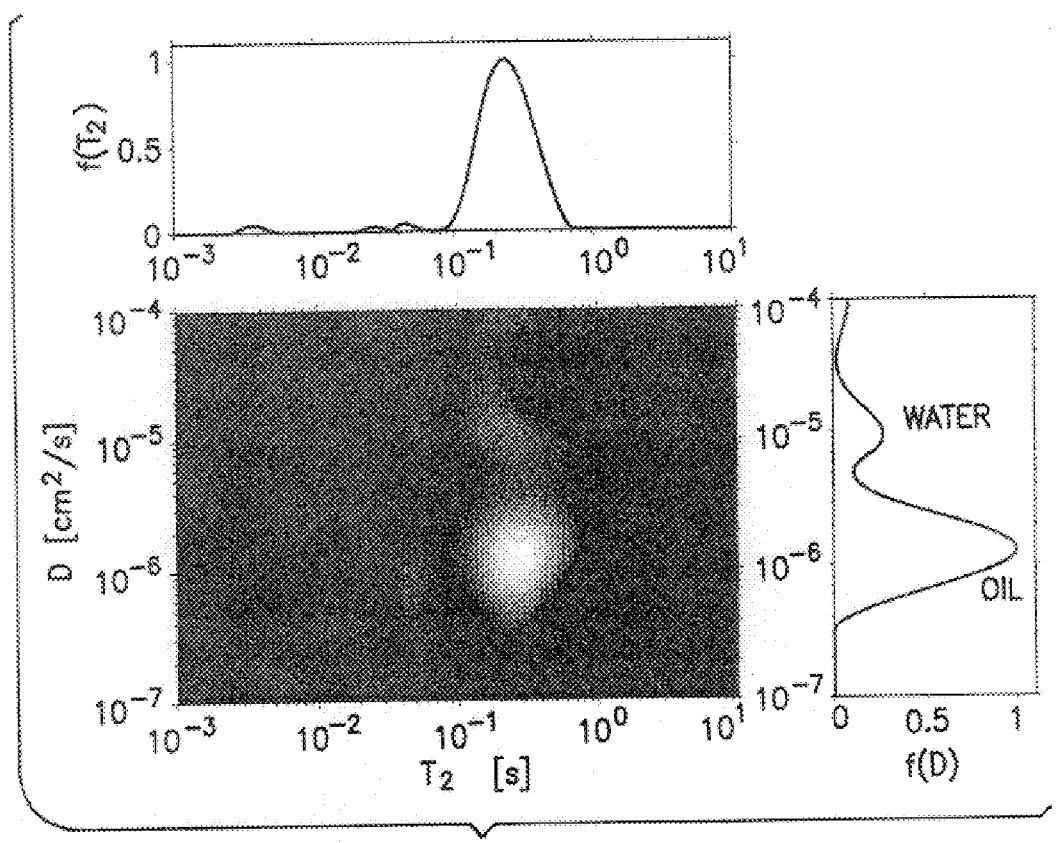
FIG. 7 shows two-dimensional plot of diffusion coefficient versus relaxation time according to certain embodiments of the invention.

FIG. 7 shows a full two-dimensional diffusion coefficient-relaxation time map, as well as corresponding one-dimensional diffusion and relaxation distributions, extracted from Equation 7 (A=0.59, B=0.20) using the data from the same partially oil saturated sandstone sample discussed above (with reference to FIG. 5). The NiCl-doped water had about the same relaxation time $T_2$ as the oil. Thus, in the conventional $T_2$ distribution shown on top (obtained by integrating $f(D,T_2)$ over D), the oil and water signals overlap completely and only a single peak appears. The two-dimensional map, as well as the diffusion distribution shown at the right (obtained by integrating $f(D,T_2)$ over $T_2$), clearly show two different diffusing components, one with a diffusion coefficient of around $10^{-6}$ cm$^2$/s that can be attributed to the S6 oil and the other with a higher diffusion coefficient of around $10^{-5}$ cm$^2$/s that can be attributed to water. The oil and water saturations correspond to the areas under the respective peaks, which were found to be 0.78 and 0.22, respectively (in good agreement with the results above).

Thus, according to one aspect of the invention, information such as diffusion coefficient and relative saturation of different components of a fluid may be determined, even if there is no contrast in relaxation times of the different components. As mentioned before, no assumptions or prior knowledge about the relationship between diffusion and relaxation are required to extract this information.

The two-dimensional map and diffusion distribution in FIG. 7 also show some contributions having an apparent diffusion coefficient that exceeds that of bulk water. These can be attributed to the effects of internal gradients within the rock sample which exceed the applied gradient of about 13 Gauss/cm. From Equation 2, it can be seen that a large internal gradient may be interpreted as a high diffusion coefficient. As mentioned above, the effects of internal gradients can be addressed using methods described elsewhere.

Figure 8:
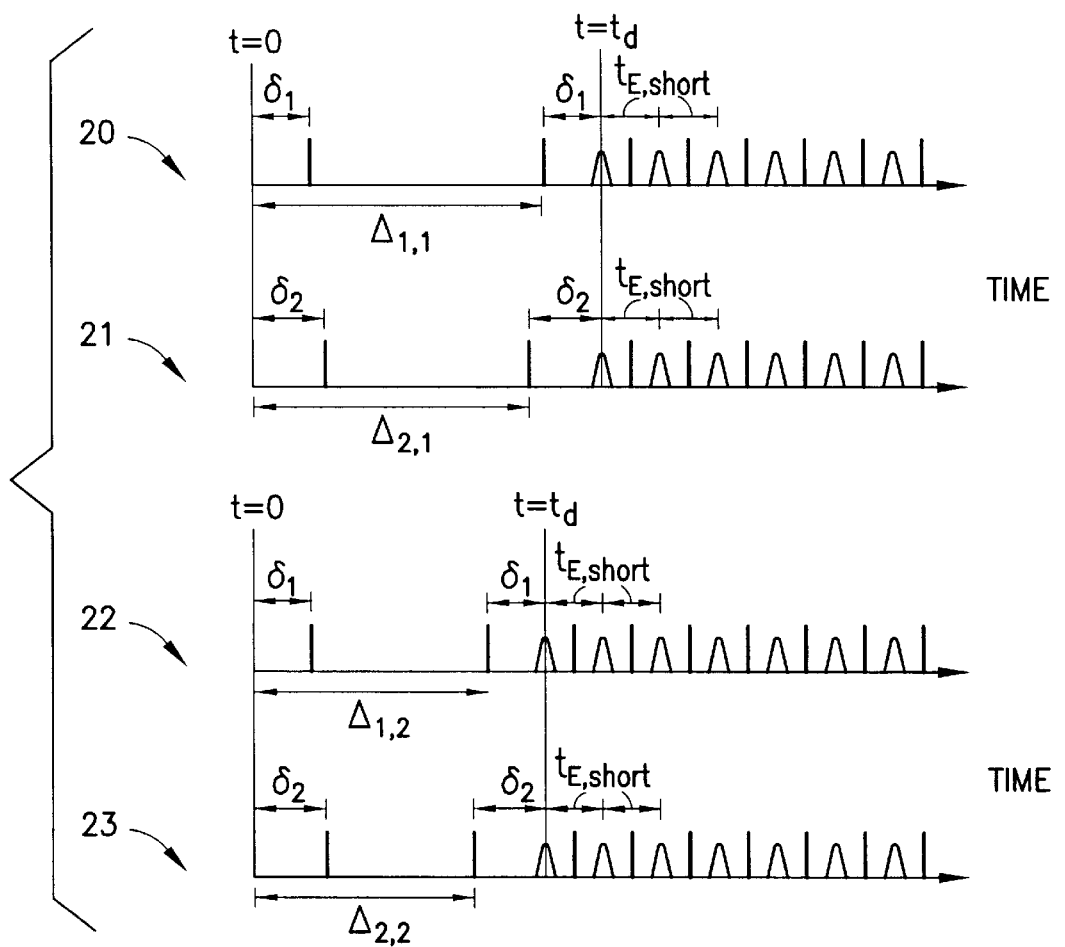
FIG. 8 illustrates a plurality of magnetic field pulse sequences that can be used in another embodiment of a NMR measurement according to the invention.

FIG. 8 illustrates a plurality of magnetic field pulse sequences that may be used in still another embodiment of an NMR measurement according to the invention. A first magnetic field pulse sequence 20 has a first portion that includes a first stimulated echo sequence. After an initial 90-degree pulse, a second 90-degree pulse is applied at time $\delta_1$ followed by a third 90-degree pulse at time $\Delta_{1,1}$, stimulating an echo at time $t_{d,1}$, at all timed being relative to the initial 90-degree pulse. A second magnetic field pulse sequence 21 is a second stimulated echo-modified CPMG sequence in which the time spacings between the initial and the second 90-degree pulses, $\delta_2$, and between the initial and third 90-degree pulses $\Delta_{2,1}$, have been modified while the time at which a stimulated echo is produced, $t_{d,1}$, is held substantially constant. A third and a fourth magnetic field pulse sequences 22 and 23, respectively, are also stimulated echo-modified CPMG sequences. In the third magnetic field pulse sequence 22, the second 90-degree pulse is generated at a time $\delta_1$ after the initial pulse, as in the first sequence 20, but the time of the stimulated echo, $t_{d,2}$, has been modified, in this case shortened. The fourth magnetic field pulse sequence 23 stimulates an echo at substantially the same time, $t_{d,2}$, while the second 90-degree pulse is generated at a time $\delta_2$ after the initial pulse, as in the second sequence 21.

Magnetic resonance signals are detected, as described previously, using the second portion of each sequence. By varying the time, $t_{d,i}$, at which data processing is started in addition to varying a time spacing in the first portion in a plurality of magnetic field pulse sequences, a time dependent attribute of the fluid in a porous medium, such as a time dependent diffusion coefficient, may be measured. For a fluid in a porous medium, such as rock or earth formation, diffusion is restricted. As diffusing spins approach the pore wall, the measured diffusion coefficient begins to deviate from the free fluid diffusion coefficient. As the spins diffuse through several pores, the diffusion coefficient asymptotically approaches a tortuosity limit given by $D_0/F\phi$, where $D_0$ is the free fluid (or bulk) diffusion coefficient, F is the electrical formation factor of the porous medium, and $\phi$ is the porosity of the medium. Thus, from the time dependent behavior of D(t), a direct indication of pore size and/or pore geometry may be determined.

Referring to the embodiment illustrated in FIG. 8, in the presence of a magnetic field gradient, the amplitude of the stimulated echo at time $t_{d,i}$ will depend on $\delta_j$ (see Equation 8, above). Thus, measuring how the amplitude of the stimulated echo varies with $\delta_j$, allows an average diffusion coefficient, $D(t_{d,i})$, for all $T_2$ components at time $t_{d,i}$ to be extracted, and varying the time $t_{d,i}$ for each time spacing $\delta_j$ allows a time dependent diffusion coefficient, $D(t)$, to be determined. It should be appreciated that other modified CPMG sequences, as described above, may be used in time dependent measurements according to the invention, with analogous analyses applied.

Figure 9:
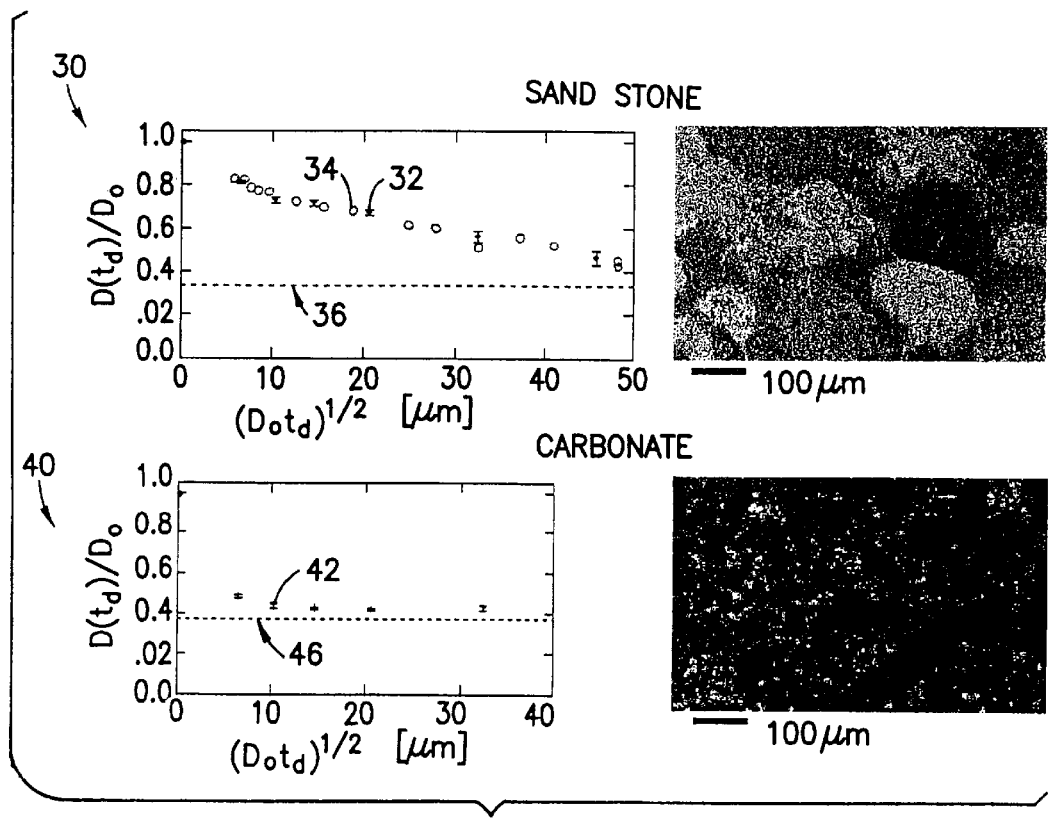
FIG. 9 shows two graphs illustrating results from two different rock samples of a time dependent diffusion coefficient measurement according to certain embodiments of the invention.

FIG. 9 contains graphs showing normalized time dependent diffusion coefficient, $D(t)/D_0$, versus diffusion length, $\sqrt{D_0 t}$, for two different rock samples. The top graph 30 illustrates restricted diffusion in a sandstone sample, while the bottom graph 40 illustrates restricted diffusion in a carbonate rock sample. Photographs of each sample are provided alongside each graph. The NMR measurements were conducted with a plurality of stimulated echo-modified CPMG sequences at times, $t_{d,i}$, 20 ms, 50 ms, 100 ms, 200 ms, 500 ms, and 1 s. For each $t_{d,i}$, five values for time spacing $\delta_j$ were used. The points with error bars, e.g., 32 and 42, are the data points generated for each $t_{d,i}$ from these measurements. The open circles, e.g., 34 in the top graph 30 show results from a conventional time dependent diffusion coefficient measurement using pulsed field gradients. The dashed lines, 36 and 46, indicate the independently determined normalized tortuosity limit, $1/F\phi$.

For the sandstone sample, the time dependent diffusion coefficient (as shown by points 32) decreases slowly and does not reach the asymptotic tortuosity limit 36 by the longest measured diffusion length (about 50 $\mu$m), indicating that the average pore size of the sandstone sample is several tens of microns. In contrast, the time dependent diffusion coefficient for the carbonate sample (as shown by points 42) approaches its tortuosity limit rapidly, indicating an average pore size of a few microns. Also, the results of the time dependent diffusion measurements of the invention on the sandstone sample 32 agree well with the results of conventional pulsed field gradient measurements 34.

Thus, in addition to information such as diffusion and saturation, the magnetic field pulse sequences of the invention may be used to extract information about pore size and pore geometry of rock without any assumptions or prior knowledge about the rock or the fluid. Conventionally, indications of pore size and pore geometry are extracted from relaxation distributions, which depends on phenomenological factors such as surface relaxivity, $\rho_2$, and surface roughness, or from time dependent diffusion measurements requiring pulsed field gradients. While the methods of the invention may be practiced with pulsed field gradients and pulsed field gradients may be used to enhance the diffusion effects in a static magnetic field, as discussed previously, pulsed field gradients are not required. The application of pulsed field gradients typically requires a large amount of power and additional hardware, such as extra RF coils, that in some settings may be undesirable.

Figure 10:
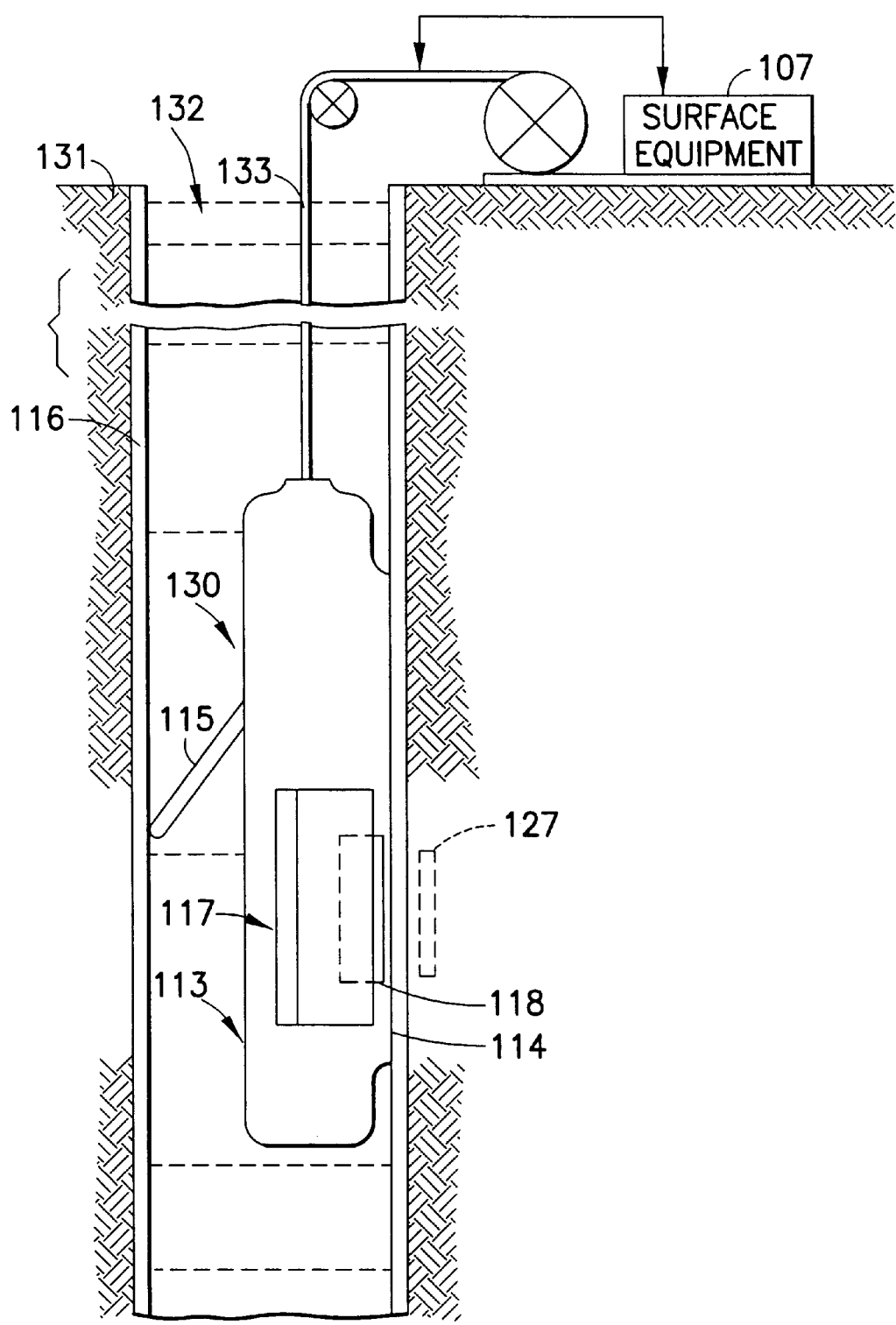
FIG. 10 is a schematic diagram, partially in block form, of one embodiment of a well logging apparatus that can be used in implementing methods according to the invention in a borehole environment.

The methods of the invention may be practiced in a laboratory setting or in a downhole environment, such as with a well logging device. FIG. 10 shows an apparatus that can be utilized for practicing embodiments of the invention to investigate subsurface formations 131 traversed by a borehole 132. A magnetic resonance investigating apparatus or logging device 130 is suspended in the borehole 132 on an armored cable 133, the length of which substantially determines the relative depth of the device 130. The length of cable 133 is controlled by suitable means at the surface such as a drum and winch mechanism. Surface equipment, represented at 107, can be of conventional type, and can include a processor subsystem that communicates with all the downhole equipment. It will be understood that some of the processing can be performed downhole and that, in some cases, some of the processing may be performed at a remote location. Also, while a wireline is illustrated, alternative forms of physical support and communicating link can be used, for example in a measurement-while-drilling or logging-while-drilling system, in practicing the methods of the invention.

As described, for example, in U.S. Pat. Nos. 5,055,787, 5,055,788, and 5,153,514, the magnetic resonance logging device 130 can have a face 114 to intimately contact the borehole wall. The borehole wall may have a mudcake 116 thereon. A retractable arm 115 is provided which can be activated to press the body of the tool 113 through the mudcake against the borehole wall during a logging run, with the face 114 pressed against the wall's surface. Although the tool 113 is shown as a single body, the tool may alternatively include separate components such as a cartridge, sonde or skid, and the tool may be combinable with other logging tools.

The logging device includes, for example, a permanent magnet or permanent magnet array 117, which may be made of a samarium-cobalt-magnetic material, and one or more RF antennas 118. The investigation region, or sensitivity zone, represented generally at 127, is a region in the formation in which the static magnetic field is generally uniform, although this is not necessarily required for operation in accordance with the invention. Some embodiments of the invention may take advantage of inherent non-uniformity in the static magnetic field to generate a static magnetic field gradient within the investigation region 127. In other embodiments, pulsed magnetic field gradients may be used to generate or enhance a magnetic field gradient within the investigation region 127. U.S. Pat. No. 5,796,252, for example, which is incorporated herein by reference, describes various embodiments of an antenna that can be incorporated into logging devices of the invention and used to produce pulse field gradients in the investigation region 127. It will be understood that other suitable tool configurations can be utilized for practicing the invention.

Figure 11:
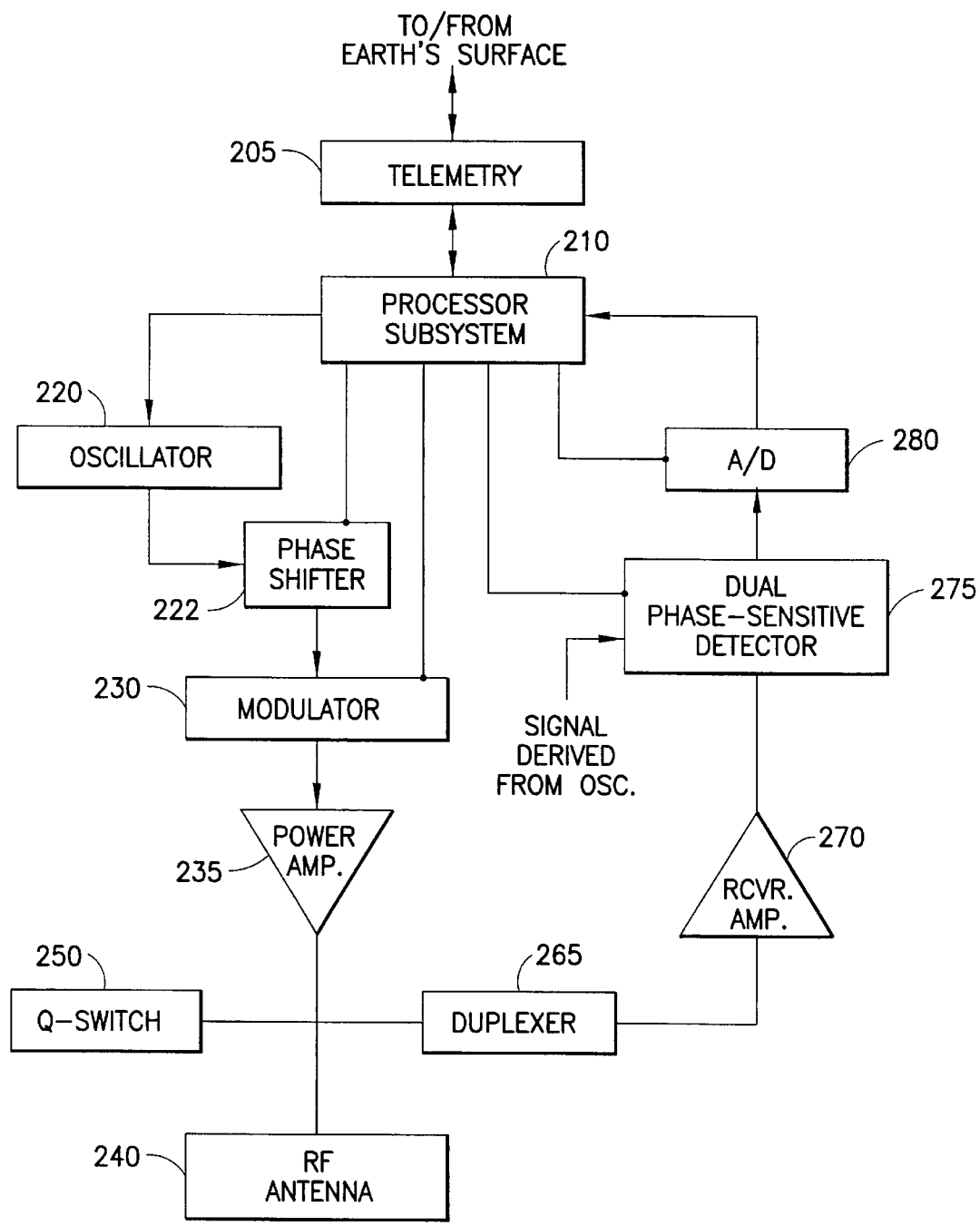
FIG. 11 is a block diagram of downhole circuitry that can be used with a well logging apparatus, such as shown in FIG. 10.

FIG. 11 shows, in simplified form, circuitry of a type that can be used for producing RF pulse sequences and for receiving and processing magnetic resonance signals; it will be appreciated, however, that circuitry having different configurations may be used for practicing the invention.

A downhole processor subsystem is represented at 210. The processor subsystem 210 has associated memory, timing, interfaces, and peripherals (not separately shown), as is known in the art. The processor subsystem is conventionally coupled with telemetry circuitry 205, for communication with the earth's surface. It should be noted that the processor subsystem and associated components may reside downhole, uphole, or partially downhole and partially uphole An oscillator 220 produces radio frequency (RF) signals at the desired resonant frequency or frequencies in the investigation region, and the output of the oscillator is coupled to a phase shifter 222 and then to a modulator 230, both of which are under control of the processor subsystem 210. The phase shifter and modulator can be controlled, in a manner known in the art, to produce the desired pulses of RF field, for example the 90-degree and 180-degree pulses utilized in embodiments hereof. As described, for example, in U.S. Pat. No. 5,055,788, the oscillator 220 can be a plurality of oscillators used in a manner that facilitates the generation and ultimate detection of the desired signals. The output of modulator 230 is coupled, via a power amplifier 235, to the RF antenna 240. A Q-switch 250 can be provided to critically dampen the RF antenna system to reduce antenna ringing.

The antenna 240 is also coupled with a receiver section via duplexer 265, the output of which is coupled to receiver amplifier 270. The duplexer 265 protects the receiver during the transmitting and damping modes. During the receiving mode, the duplexer 265 is effectively just a low impedance connection from the antenna to the receiver amplifier 270. The output of the receiver amplifier 270 is coupled to a dual phase-sensitive detector 275, which also receives, as a reference, a signal derived from the oscillator signal. The detected output is coupled to analog-to-digital converter 280, the output of which is a digital version of the received nuclear magnetic resonance signal.

Figure 12A:
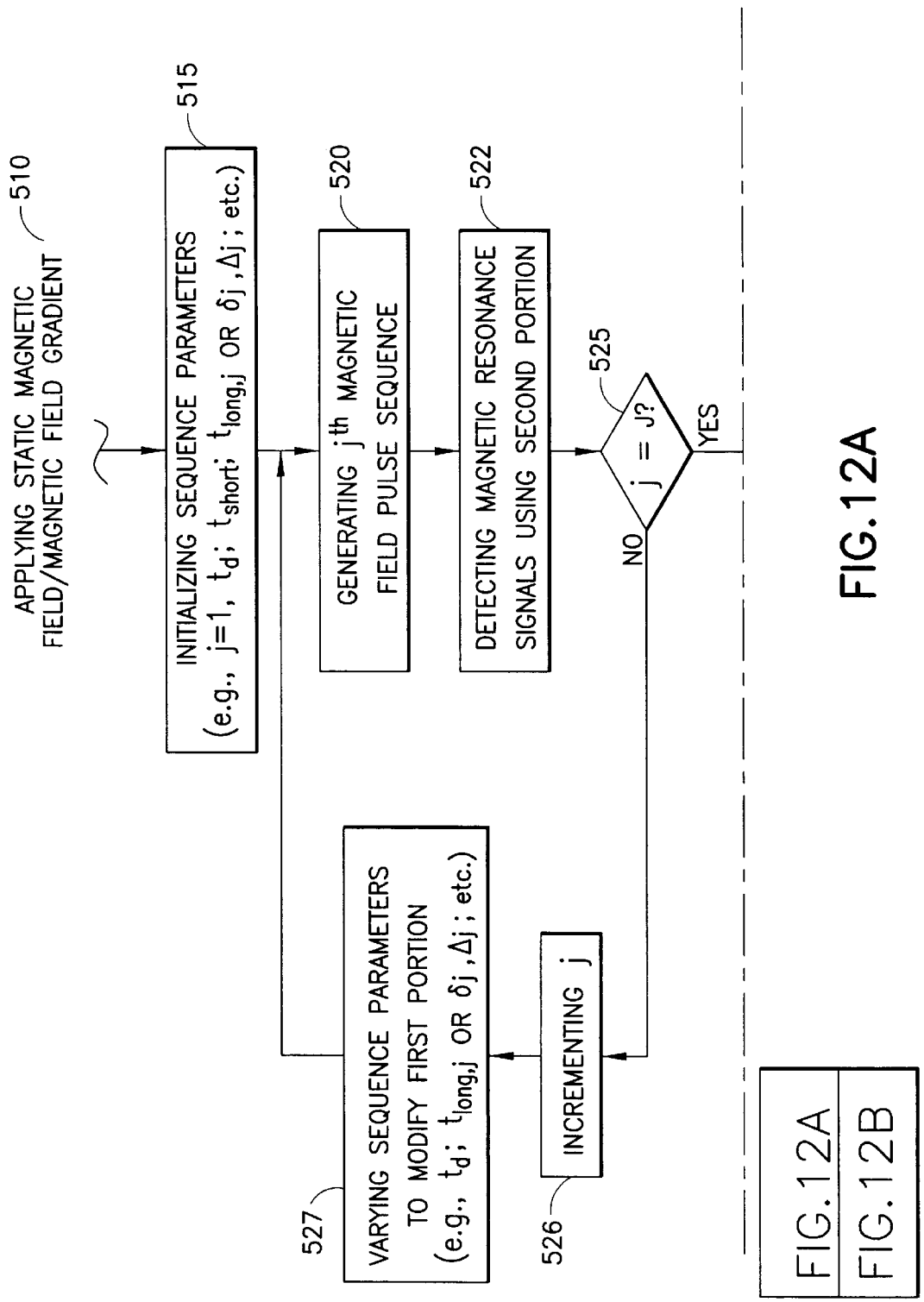
FIG. 12 is a flow diagram of a routine that can be used in programming a processor or processors in implementing certain embodiments of the invention.
Figure 12B:
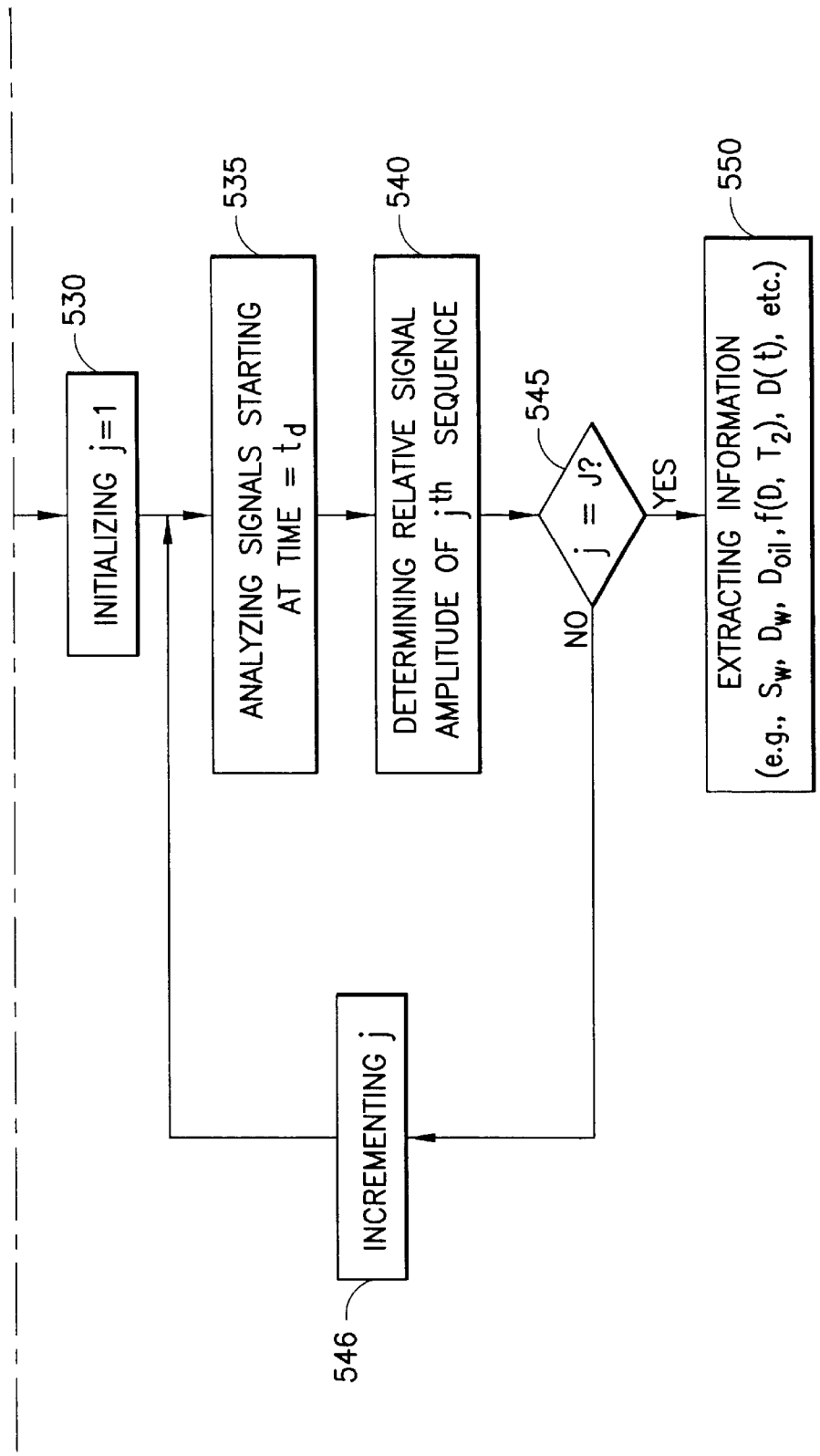

Embodiments of the invention may be implemented with logging devices, such as those described above, without the need for any hardware modifications. FIG. 12 shows a flow diagram of a routine that can be used in programming a processor in implementing embodiments of the invention. The routine may be stored on or provided over a computer or machine readable medium, such as read-only memory (ROM); random access memory (RAM); magnetic disc or tape; a CD-ROM or other optical storage media; electrical, optical, acoustical or other forms of propagated signals; and the like. The processor may be a downhole processor, an uphole processor, or a combination thereof. The processor also may include a remote processor that may be used for implementing some of the data interpretation parts of the routine.

Prior to the beginning of the programmed routine and as shown at 510, a static magnetic field and, for certain embodiments, a static magnetic field gradient are applied to a region of investigation of earth formation surrounding a borehole. Theoretically, the earth's magnetic field could be used as the static magnetic field, and internal field gradients present within the earth formation could be used as the static magnetic field gradient. For most practical purposes, however, these are not preferred. The static magnetic field and field gradient typically are applied using a logging tool having a permanent magnet or an array of permanent magnets, as described above. Also, in some embodiments, pulsed magnetic field gradients may be applied to the region of investigation from the logging tool. Logging tools can typically generate static magnetic field gradients in a range of about 10 to 80 Gauss/cm, but embodiments of this invention may be implemented with gradients outside this range.

The programmed routine begins at block 515, which represents initializing parameters for the magnetic field pulse sequences used in the invention. The sequence parameters may include, for example, $j=1$, $t_{short}$, $t_d$, $t_{long,j}$ or $\delta_j$ and $\Delta_j$, depending on the pulse sequence to be applied. Other sequence parameters may be used instead of, or in addition to, the parameters listed (for example, a number (m,j) may be used to track the number of spin echoes in the first portion, an index, $i=1$, may be initialized to track different times $t_{d,i}$, etc.), and the sequence parameters may be initialized all together or at different points in the routine as needed.

Generating a magnetic field pulse sequence in the region of investigation is represented by block 520. The magnetic field pulse sequences used in the invention include an initial magnetic field pulse, a first portion and a second portion. Magnetic resonance signals from the region of investigation are detected using the second portion of the magnetic field pulse sequence in block 522 and stored. In some embodiments, all magnetic resonance signals from the region of investigation may be detected and stored. In other embodiments, magnetic resonance signals preceding a time $t_d$ after the initial pulse of the sequence may not be detected, or signals corresponding to time$<t_d$ may be detected but not stored, or stored and later discarded, or stored and processed in a separate analysis.

The methods of the invention involve at least two magnetic field pulse sequences with differing first portions. A parameter J may be used (set, perhaps, at block 515) to indicate a total number of magnetic field pulse sequences to be generated. Decision block 525 represents querying whether $j=J$. If no, then j is incremented, as represented in block 526, and sequence parameters, such as $t_{long,j}$, or $\delta_j$ and $\Delta_j$, or $t_d$, are varied to modify the first portion of the sequence as represented in block 527, before the routine is returned to block 520 where the next sequence is generated in the region of investigation. If $j=J$ when queried at decision block 525, then the data acquisition for the measurement is complete and the routine continues on to block 530 where j is re-initialized to $j=1$.

In some embodiments of the invention, two or more sequence parameters, for example, $\delta_j$ and $t_{d,i}$, or $t_{long,j}$ and $t_{d,i}$, are varied sequentially, such that, for each time $t_{d,i}$, a plurality of magnetic field pulse sequences are generated in the region of investigation using a set of different time spacings, e.g., $\delta_j$ or $t_{long,j}$. Then, time $t_{d,i}$ would be incremented, and a second plurality of magnetic field pulse sequences using the same set of time spacings is generated in the region of investigation. To implement such embodiments would require initializing an additional parameter, $i=1$ (perhaps at block 515), and introducing an additional loop into the routine shown in FIG. 12 around, for example, blocks 515 and 530. After all the pluralities of magnetic field pulse sequences have been generated and magnetic resonance signals detected and stored, the parameter, i, would be re-initialized to $i=1$ before the routine proceeds.

Blocks 535 and 540 represent, respectively, analyzing the stored magnetic resonance signals starting at time $t_d$ and determining a relative amplitude of the $j^{th}$ sequence signal. The relative amplitude of the signal may be quantified as an attenuation factor, or the entire data set may be stored for later analysis. Block 545 represents querying whether all J sequences have been analyzed. If no, parameter j is incremented as indicated by block 546 and blocks 535 and 540 repeated until $j=J$. For embodiments of the invention involving an additional set of parameters, such as times, $t_{d,i}$, an additional loop would be introduced into the routine around, for example, block 535, or around blocks 535 and 545, to analyze the stored signals with respect to that parameter.

When all the relative amplitude data have been calculated, the amplitude data is used to extract information about the fluid, as represented by block 550. As discussed above, extracting information such as diffusion coefficient, saturation, fluid composition, etc. may involve calculating an attenuation factor; or fitting the amplitude data to an equation such as Equation 6, 7, or 8 and extracting information from the fit; or extracting a full two-dimensional map and identifying different components and other information from the map; or combinations of such analyses. Additionally, information such as pore size or an indication of pore geometry may be extracted from the time dependent behavior of an attribute, such as diffusion coefficient, which also can be extracted from the analyzed amplitude data.

The invention has been described herein with reference to certain examples and embodiments. It will, however, be evident that various modifications and changes may be made to the embodiments described above without departing from the scope of the invention as claimed.

We claim:

1. A method of extracting information by determining diffusion and relaxation characteristics about a fluid in a rock using nuclear magnetic resonance (NMR) comprising:
   a) generating a sequence of magnetic field pulses in the fluid, the sequence comprising at least one initial magnetic field pulse, a first portion that follows the at least one initial magnetic field pulse, and a second portion that follows the first portion such that the second portion refocuses the last echo of the first portion;
   b) detecting magnetic resonance signals using the sequence;
   c) manipulating the sequence by modifying the first portion and repeating steps a) and b); and
   d) extracting information about the fluid in the rock by determining relaxation and diffusion characteristics and their correlation based on the signals detected in steps (b) and (c).

2. The method of claim 1, wherein the second portion comprises a series of magnetic field pulses separated by a time spacing.

3. The method of claim 2, wherein the first portion comprises a first series of magnetic field pulses separated by a first time spacing.

4. The method of claim 3, wherein the first time spacing is not less than the time spacing of the second portion.

5. The method of claim 2, wherein the first portion comprises a stimulated echo sequence.

6. The method of claim 1, wherein the first portion includes at least one magnetic field gradient pulse.

7. The method of claim 1, wherein modifying the first portion comprises varying a time spacing between magnetic field pulses.

8. The method of claim 1, wherein analyzing magnetic resonance signals comprises calculating an attenuation factor.

9. The method of claim 1, wherein analyzing magnetic resonance signals comprises determining a relative amplitude of the magnetic resonance signals.

10. The method of claim 1, wherein extracting information about the fluid comprises determining a diffusion coefficient.

11. The method of claim 1, wherein extracting information about the fluid comprises distinguishing between different components of the fluid.

12. The method of claim 1, wherein extracting information about the fluid comprises determining a saturation of the fluid in the rock.

13. The method of claim 1, further comprising:
   e) repeating step c) a plurality of times.

14. The method of claim 13, wherein extracting information about the fluid comprises extracting a two dimensional map of a first parameter indicative of the fluid in the rock versus a second parameter indicative of the fluid in the rock.

15. The method of claim 14, wherein the first parameter is a diffusion coefficient.

16. The method of claim 14, wherein a second parameter is a relaxation time.

17. The method of claim 13, further comprising:
   f) varying the time relative to the initial magnetic field pulse from which the magnetic resonance signals are analyzed and repeating steps a) through e).

18. The method of claim 17, further comprising repeating step f) a plurality of times.

19. The method of claim 17, wherein extracting information about the fluid comprises determining a time dependent diffusion coefficient.

20. The method of claim 17, further comprising determining an indication of pore geometry of the rock.

21. A method of extracting information by determining diffusion and relaxation characteristics about a fluid in a rock using nuclear magnetic resonance (NMR) comprising:
   a) generating a first sequence of magnetic field pulses in the fluid, the first sequence comprising at least one initial magnetic field pulse, a first portion followed by a second portion, such that the second portion refocuses the last echo of the first portion;
   b) detecting magnetic resonance signals using the first sequence;
   c) manipulating the first sequence to generate at least one additional sequence of magnetic field pulses in the fluid, each additional sequence comprising at least one initial magnetic field pulse, a third portion followed by a fourth portion, such that the fourth portion refocuses the last echo of the third portion, the third portion having a different sensitivity to diffusion effects than the first portion of the first sequence and the fourth portion having a similar sensitivity to diffusion effects as the second portion of the first sequence;
   d) detecting magnetic resonance signals using each additional sequence generated in step (c); and
   e) analyzing magnetic resonance signals to separate diffusion effects from relaxation effects about the fluid in the rock using the detected signals of steps (b) and (d).

22. The method of claim 21, wherein the first portion of the first sequence is substantially similar to the second portion of the first sequence.

23. The method of claim 22, wherein the first sequence of magnetic field pulses is generated according to:

$$90-[t_{short}-180-t_{short}-\text{echo}_i]_n$$

wherein $t_{short}$ is a time spacing; $\text{echo}_i$ is the $i^{th}$ magnetic resonance spin echo; and n is the number of spin echoes.

24. The method of claim 21, wherein the first sequence comprises a modified CPMG sequence.

25. The method of claim 24, wherein the first sequence is generated according to:

$$90-[t_{long}-180-t_{long}-\text{echo}_k]_m-[t_{short}-180-t_{short}-\text{echo}_{i'}]_{n'}$$

wherein $t_{long}$ is a first time spacing; $\text{echo}_k$ is the $k^{th}$ magnetic resonance spin echo of the first portion; m is the number of spin echoes of the first portion; $t_{short}$ is a second time spacing, the second time spacing being shorter than the first time spacing; $\text{echo}_{i'}$ is the $i'^{th}$ magnetic resonance spin echo of the second portion; and n' is the number of spin echoes of the second portion.

26. The method of claim 24, wherein the first sequence is generated according to:

$$90-[\delta-90-(\Delta-\delta)-90-\delta-\text{echo}_k]_m-[t_{short}-180-t_{short}-\text{echo}_{i'}]_{n'}$$

wherein $\delta$ and $\Delta$ are time spacings in the first portion; $\text{echo}_k$ is the $k^{th}$ stimulated magnetic resonance spin echo of the first portion; m is the number of stimulated spin echoes of the first portion; $t_{short}$ is a time spacing in the second portion; $\text{echo}_{i'}$ is the $i'^{th}$ magnetic resonance spin echo of the second portion; and n' is the number of spin echoes of the second portion.

27. The method of claim 21, wherein the other sequence comprises a modified CPMG sequence.

19

28. The method of claim 27, wherein at least one other sequence is generated according to:

$$90-[t_{long,j}-180-t_{long,j}-echo_{k,j}]_{m,j}-[t_{short}-180-t_{short}-echo_{i',j}]_{n',j}$$

wherein, for the $j^{th}$ other sequence, $t_{long,j}$ is a third time spacing; $echo_{k,j}$ is the $k^{th}$ magnetic resonance spin echo of the third portion; (m,j) is the number of spin echoes of the third portion; $t_{short}$ is a fourth time spacing, the fourth time spacing being shorter than the third time spacing; $echo_{i',j}$ is the $i'^{th}$ magnetic resonance spin echo of the fourth portion; and (n',j) is the number of spin echoes of the fourth portion.

29. The method of claim 27, wherein at least one other sequence is generated according to:

$$90-[\delta_j-90-(\Delta_j-\delta_j)-90-\delta_j-echo_{k,j}]_{m,j}-[t_{short}-180-t_{short}-echo_{i',j}]_{n',j}$$

wherein, for the $j^{th}$ other sequence, $\delta_j$ and $\Delta_j$ are time spacings in the third portion; $echo_{k,j}$ is the $k^{th}$ stimulated magnetic resonance spin echo of the third portion; (m,j) is the number of stimulated spin echoes of the third portion; $t_{short}$ is a time spacing in the fourth portion; $echo_{i',j}$ is the $i'^{th}$ magnetic resonance spin echo of the fourth portion; and (n',j) is the number of spin echoes of the fourth portion.

30. The method of claim 21, wherein the first portion and the third portion include at least one magnetic field gradient pulse.

31. The method of claim 21, wherein analyzing magnetic resonance signals comprises determining an amplitude of the signal from the other sequence relative to an amplitude of the signal from the first sequence.

32. The method of claim 21, wherein analyzing magnetic resonance signals comprises analyzing spin echoes from the first sequence that correspond in time to spin echoes from the other sequence.

33. The method of claim 21, wherein analyzing magnetic resonance signals comprises analyzing a substantially equal number of spin echoes from the first sequence and from the other sequence.

34. The method of claim 21, further comprising extracting a two-dimensional map of two parameters indicative of the fluid in the rock.

35. The method of claim 21, further comprising generating a static magnetic field gradient in the rock.

36. The method of claim 35, further comprising:
f) moving the rock and the static magnetic field gradient relative to each other; and
g) repeating steps a) through f) a plurality of times to obtain a profile of an attribute through at least part of the rock.

37. The method of claim 21, wherein analyzing magnetic resonance signals comprises correlating spin echoes from the first sequence in time with spin echoes from the other sequence and analyzing correlated spin echoes at a given time, and further comprising:
f) varying the given time at which correlated spin echoes are analyzed, and
g) repeating steps a) through f) a plurality of times.

38. The method of claim 37, further comprising determining a time dependent attribute of the fluid in the rock.

39. The method of claim 37, further comprising determining an indication of a pore geometry of the rock.

40. A method of extracting information by determining diffusion and relaxation characteristics about a fluid in the rock using nuclear magnetic resonance (NMR) comprising:
a) generating a first sequence of magnetic field pulses in the fluid, the first sequence comprising at least one

20 initial magnetic field pulse, a first series of magnetic field pulses with a first time spacing;
b) detecting echoes using the first sequence;
c) manipulating the first sequence to generate a second sequence of magnetic field pulses in the fluid, the second sequence comprising at least one initial magnetic field pulse, a second series followed by a third series, such that the third series refocuses the last echo of the second series, and wherein the second series has a time spacing greater than the first time spacing and the third series has a time spacing equal to the first time spacing;
d) detecting echoes using the second sequence;
e) extracting information about the fluid in the rock using echoes detected in steps (b) and (d) by determining relaxation and diffusion characteristics and their correlation.

41. The method of claim 40, wherein extracting information comprises analyzing spin echoes detected using the first series that correspond in time to spin echoes detected using the third series.

42. The method of claim 40, wherein extracting information comprises analyzing a substantially equal number of spin echoes detected using the first series and the third series.

43. The method of claim 40, wherein extracting information comprises determining an amplitude of the spin echoes detected using the third series relative to an amplitude of the spin echoes detected using the first series.

44. The method of claim 40, further comprising:
f) generating at least one other sequence of magnetic field pulses in the fluid, each other sequence comprising a fourth series of magnetic field pulses with a time spacing greater than the first time spacing and different from the second time spacing and from each other, and a fifth series of magnetic field pulses with the first time spacing; and
g) detecting spin echoes using the fifth series, wherein information about the fluid is extracted using the spin echoes detected using the first series, the third series, and the fifth series.

45. The method of claim 44, wherein extracting information comprises analyzing spin echoes detected using the first series that correspond in time to spin echoes detected using the fifth series.

46. The method of claim 44, wherein extracting information comprises analyzing a substantially equal number of spin echoes detected using the first series and the fifth series.

47. The method of claim 44, wherein extracting information comprises extracting a two-dimensional function of a first parameter and a second parameter indicative of the fluid in rock.

48. The method of claim 47, wherein the first parameter is a diffusion coefficient and the second parameter is a relaxation time.

49. A logging apparatus to extract information by determining diffusion and relaxation characteristics about a region of investigation using nuclear magnetic resonance (NMR) comprising:
a logging tool that is moveable through a borehole; and
a processor that is coupled with the logging tool, the processor being programmed with instructions which, when executed by the processor:

cause the logging tool to:
  i) generate a sequence of magnetic field pulses in a region of investigation of earth formation surrounding a borehole, the sequence comprising at least one initial magnetic field pulse, a first portion followed by a second portion, such that the second portion refocuses the last echo of the first portion;
  ii) detect magnetic resonance signals produced from the region of investigation using the sequence;
  iii) manipulate the sequence by modifying the first portion of the sequence, and repeat steps (i) and (ii); and cause the processor to:
  iv) extract information about the region of investigation by determining relaxation and diffusion characteristics and their correlation based on the signals detected in (ii) and (iii).

50. The logging apparatus of claim 49, wherein the second portion comprises a series of magnetic field pulses separated by a time spacing.

51. The logging apparatus of claim 49, wherein the first portion comprises a first series of magnetic field pulses separated by a first time spacing.

52. The logging apparatus of claim 49, wherein the first portion comprises a stimulated echo sequence.

53. The logging apparatus of claim 49, wherein the instructions, when executed by the processor, cause the logging tool to: v) repeat step iii) a plurality of times.

54. The logging apparatus of claim 53, wherein the instructions, when executed by the processor, cause the processor to extract a two-dimensional function of two parameters that characterize the region of investigation.

55. The logging apparatus of claim 53, wherein the instructions, when executed by the processor, cause the processor to vary the time relative to the initial magnetic field pulse from which the magnetic resonance signals are analyzed and repeat steps i) through v).

56. A logging apparatus to extract information by determining diffusion and relaxation characteristics using nuclear magnetic resonance (NMR) comprising:
  a logging tool that is moveable through a borehole; and
  a processor that is coupled with the logging tool, the processor being programmed with instructions which, when executed by the processor:
  cause the logging tool to:
    i) generate a first sequence of magnetic field pulses in the region of investigation of earth formation surrounding a borehole, the first sequence comprising at least one initial magnetic field pulse, a first portion followed by a second portion, such that the second portion refocuses the last echo of the first portion;
    ii) detect echoes produced from the region of investigation using the first sequence;
    iii) generate at least one additional sequence of magnetic field pulses in the region of investigation, each additional sequence comprising at least one initial magnetic field pulse, a third portion followed by a fourth portion such that the fourth portion refocuses the last echo of the third portion, the third portion having a different sensitivity to diffusion effects than the first portion of the first sequence and the fourth portion having a similar sensitivity to diffusion effects as the second portion of the first sequence;
    iv) detect echoes produced from the region of investigation of each additional sequence of step (iii); and cause the processor to:
    v) analyze detected echoes to separate diffusion effects from relaxation effects of the region of investigation using the signals detected in (ii) and (iv).

57. The logging apparatus of claim 56, wherein the first portion of the first sequence is substantially similar to the second portion of the first sequence.

58. The logging apparatus of claim 57, wherein the first sequence comprises a CPMG sequence.

59. The logging apparatus of claim 56, wherein the first sequence comprises a modified CPMG sequence.

60. The logging apparatus of claim 56, wherein the other sequence comprises a modified CPMG sequence.

61. The logging apparatus of claim 56, wherein the instructions, when executed by the processor, cause the processor to analyze a substantially equal number of spin echoes detected using the second portion of the first sequence and detected using the fourth portion of the other sequence.

62. The logging apparatus of claim 56, wherein the instructions, when executed by the processor, cause the processor to analyze spin echoes detected using the second portion that correspond in time to spin echoes detected using the fourth portion.

63. The logging apparatus of claim 56, wherein step v) involves analyzing spin echoes at a given time, and the instructions, when executed by the processor, cause the processor to vary the given time.

64. A logging apparatus to extract information by determining diffusion and relaxation characteristics using nuclear magnetic resonance (NMR) comprising:
  means for generating a sequence of magnetic field pulses in the region of investigation of earth formation of a borehole, the sequence comprising at least one initial magnetic field pulse, a first portion followed by a second portion, such that the second portion refocuses the last echo of the first portion;
  means for detecting magnetic resonance signals using the sequence;
  means for manipulating the sequence by modifying the first portion; and
  means for analyzing magnetic resonance signals from a time relative to the at least one initial magnetic field pulse to extract information about the region of investigation by determining relaxation and diffusion characteristics and their correlation.

65. The logging apparatus of claim 64, further comprising means for generating magnetic field gradient pulses in the region of investigation.

66. A logging apparatus to extract information by determining diffusion and relaxation characteristics using nuclear magnetic resonance (NMR) comprising:
  means for generating a first sequence of magnetic field pulses in the region of investigation of earth formation of a borehole, the first sequence comprising at least one initial magnetic field pulse, a first portion followed by a second portion, such that the second portion refocuses the last echo of the first portion;
  means for detecting magnetic resonance signals from the region of investigation using the first sequence;
  means for generating at least one additional sequence of magnetic field pulses in the region of investigation, each additional sequence comprising at least one initial magnetic field pulse, a third portion followed by a fourth portion, such that the fourth portion refocuses the last echo of the third portion, the third portion having a different sensitivity to diffusion effects than the first portion of the first sequence and the fourth portion having a similar sensitivity to diffusion effects as the second portion of the first sequence;

means for detecting magnetic resonance signals from the region of investigation using each additional sequence; and means for analyzing magnetic resonance signals to separate diffusion effects from surface and bulk relaxation effects of the region of investigation using the detected signals.

67. The logging apparatus of claim 66, further comprising means for generating magnetic field gradient pulses in the region of investigation.

* * * * *